(12) United States Patent
Blinkovsky et al.

(10) Patent No.: US 6,187,578 B1
(45) Date of Patent: Feb. 13, 2001

(54) CARBOXYPEPTIDASES AND NUCLEIC ACIDS ENCODING THE SAME

(75) Inventors: Alexander Blinkovsky; Randy Berka; Michael Rey; Elizabeth Golightly, all of Davis; Alan Klotz, Dixon, all of CA (US); Thomas Erik Mathisen, Copenhagen; Claus Dambmann, Søborg, both of (DK); Kimberly M. Brown, Elk Grove, CA (US)

(73) Assignees: Novo Nordisk Biotech, Inc., Davis, CA (US); Novo Nordisk A/S, Bogsvoerd (DK)

( * ) Notice: Under 35 U.S.C. 154(b), the term of this patent shall be extended for 0 days.

(21) Appl. No.: 08/943,714

(22) Filed: Oct. 3, 1997

Related U.S. Application Data

(63) Continuation-in-part of application No. PCT/DK97/00230, filed on May 20, 1997, which is a continuation-in-part of application No. 08/757,534, filed on Nov. 27, 1996, now abandoned, which is a continuation-in-part of application No. 08/726,880, filed on Oct. 4, 1996, now abandoned.

(30) Foreign Application Priority Data

May 20, 1996 (DK) .................................................... 0585/96

(51) Int. Cl.[7] .................................................. G12N 9/48
(52) U.S. Cl. ............................................................ 435/212
(58) Field of Search ............................................. 435/212

(56) References Cited

FOREIGN PATENT DOCUMENTS

WO 96/09397    3/1996  (WO) .

OTHER PUBLICATIONS

Choi et al. "Partial characterization of *Aspergillus oryzae* cell wall fraction–bound enzyme related to immobilized biocatalyst" Journal of Fermentation and Bioengineering, 1991,vol. 72, No. 3, pp. 216–216), Aug. 15, 1991.*

Choi et al., Journal of Fermentation and Bioengineering, vol. 72 No. 3, pp. 214–216. (1991).

Azarenkova et al., Biochemistry, vol. 41, No. 1/1, pp. 15–21 (1976).

Svensen et al., FEBS Letters, vol. 333, No. 1/2, pp. 39–43 (1993).

Database WPI, XP 002054568, JP 54 037 894 (Tanabe Seiyaku) No Date Provided.

Database WPI, XP 002054569 JP 48 035 459 (Kikkoman Shoyu KK) No Date Provided).

Ichishima et al., J. Biochem., 1972, vol. 72, pp. 1045–1048.*

* cited by examiner

*Primary Examiner*—Ponnathapu Achutamurthy
*Assistant Examiner*—Bradley S. Mayhem
(74) *Attorney, Agent, or Firm*—Robert L. Starnes; Elias Lambins, Esq.

(57) ABSTRACT

The present invention relates to polypeptides having carboxypeptidase activity and isolated nucleic acid sequences encoding the polypeptides. The invention also relates to nucleic acid constructs, vectors, and host cells comprising the nucleic acid sequences as well as methods for producing the polypeptides. The present invention further relates to methods of obtaining protein hydrolysates useful as flavor improving agents.

12 Claims, 5 Drawing Sheets

```
ATGCGTGGCTACGAATTTCTCTCAGTGCTACCCTTGGTTGCAGCCAGTTGGGCCCTTCCAGGAAGTACAC  70
 M  R  G  Y  E  F  L  S  V  L  P  L  V  A  A  S  W  A  L  P  G  S  T
CGGCGTCCGTCGGTAGAAGACAGCTACCCAAGAACCCCACCGGGGTCAAGACTCTTACAACCGCAAACAA 140
 P  A  S  V  G  R  R  Q  L  P  K  N  P  T  G  V  K  T  L  T  T  A  N  N
TGTCACCATCCGGTACAAGGAACCCGGGGCAGAGGGCGTCTGCGAGACTACCCCGGGTGTCAAATCCTAC 210
   V  T  I  R  Y  K  E  P  G  A  E  G  V  C  E  T  T  P  G  V  K  S  Y
TCTGGATATGTCGACACCTCTCCCGAGTCCCATACCTTCTTCTGGTTCTTCGAAGCCAGACATAACCCAG 280
   S  G  Y  V  D  T  S  P  E  S  H  T  F  F  W  F  F  E  A  R  H  N  P
AAACTGCACCTATCACATTGTGGTTGAATGGTGGCCCTGGAAGCGATTCTTTGATCGGTCTCTTCGAAGA 350
   E  T  A  P  I  T  L  W  L  N  G  G  P  G  S  D  S  L  I  G  L  F  E  E
GTTGGGCCCTTGCCATGTCAATTCGACTTTTGATGACTACATCAACCCTCACTCGTGGAACGAGGTCTCC 420
   L  G  P  C  H  V  N  S  T  F  D  D  Y  I  N  P  H  S  W  N  E  V  S
AATTTACTATTCCTGTCCCAGCCATTGGGAGTCGGCTTTTCATATAGTGATACGGTTGATGGGTCCATTA 490
   N  L  L  F  L  S  Q  P  L  G  V  G  F  S  Y  S  D  T  V  D  G  S  I
ACCCTGTAACTGGGGTCGTCGAAAATTCGAGCTTTGCAGGAGTTCAGGGCCGGTACCCAACCATTGATGC 560
   N  P  V  T  G  V  V  E  N  S  S  F  A  G  V  Q  G  R  Y  P  T  I  D  A
CACTCTGATCGATACTACCAATCTTGCCGCAGAGGCCGCTTGGGAGATCCTGCAAGGATTCCTTAGTGGA 630
   T  L  I  D  T  T  N  L  A  A  E  A  A  W  E  I  L  Q  G  F  L  S  G
CTACCTAGCTTGGACTCTAGGGTGCAGTCTAAGGACTTCAGTCTATGGACGGAGAGCTATGGAGGGCACT 700
   L  P  S  L  D  S  R  V  Q  S  K  D  F  S  L  W  T  E  S  Y  G  G  H
ATGGTCCTGCATTCTTCAATCATTTTTACGAGCAGAATGAGAGAATTGCCAACGGTAGTGTTAATGGTGT 770
   Y  G  P  A  F  F  N  H  F  Y  E  Q  N  E  R  I  A  N  G  S  V  N  G  V
TCAGCTTAATTTCAACTCTCTGGGAATTATTAACGGCATCATCGACGAGGCGATCCAGGCCCCTTACTAC 840
   Q  L  N  F  N  S  L  G  I  I  N  G  I  I  D  E  A  I  Q  A  P  Y  Y
CCTGAATTCGCTGTGAACAATACCTACGGTATCAAGGCTGTCAACGAGACCGTCTACAACTACATGAAGT 910
   P  E  F  A  V  N  N  T  Y  G  I  K  A  V  N  E  T  V  Y  N  Y  M  K
TTGCCAACCAAATGCCAAATGGTTGCCAGGATTTGATTTCCACCTGCAAACAGACAAACCGCACCGCATT 980
   F  A  N  Q  M  P  N  G  C  Q  D  L  I  S  T  C  K  Q  T  N  R  T  A  L
AGCTGACTACGCCCTCTGCGCCGAAGCCACCAACATGTGCAGGGACAATGTTGAGGGGCCATACTACGCC 1050
   A  D  Y  A  L  C  A  E  A  T  N  M  C  R  D  N  V  E  G  P  Y  Y  A
TTTGCTGGTCGTGGTGTGTATGATATTCGGCATCCATATGATGACCCGACTCCGCCAAGTTATTACAACA 1120
   F  A  G  R  G  V  Y  D  I  R  H  P  Y  D  D  P  T  P  P  S  Y  Y  N
AATTTCTGGCAAAGGACTCTGTCATGGACGCTATCGGCGTCAACATCAACTACACCCAGTCCAATAATGA 1190
   K  F  L  A  K  D  S  V  M  D  A  I  G  V  N  I  N  Y  T  Q  S  N  N  D
CGTCTACTACGCTTTCCAGCAAACAGGCGACTTTGTCTGGCCCAACTTCATCGAAGACCTCGAGGAGATC 1260
   V  Y  Y  A  F  Q  Q  T  G  D  F  V  W  P  N  F  I  E  D  L  E  E  I
CTTGCTCTCCCCGTGCGTGTCTCCCTCATCTATGGCGACGCCGATTACATCTGCAACTGGTTCGGCGGTC 1330
   L  A  L  P  V  R  V  S  L  I  Y  G  D  A  D  Y  I  C  N  W  F  G  G
AGGCCGTTTCCCTCGCTGCGAACTACTCCCAAGCCGCCCAGTTCCGAAGCGCAGGGTACACGCCCCTGAA 1400
   Q  A  V  S  L  A  A  N  Y  S  Q  A  A  Q  F  R  S  A  G  Y  T  P  L  K
AGTCAACGGCGTCGAGTATGGGGAAACTCGCGAGTATGGTAATTTCTCCTTCACTCGCGTCTATGAGGCA 1470
   V  N  G  V  E  Y  G  E  T  R  E  Y  G  N  F  S  F  T  R  V  Y  E  A
GGCCATGAAGTCCCATACTACCAGCCCATCGCCTCCCTGCAATTGTTTAACCGGACTATCTTCGGTTGGG 1540
   G  H  E  V  P  Y  Y  Q  P  I  A  S  L  Q  L  F  N  R  T  I  F  G  W
ATATCGCAGAGGGCCAGAAGAAGATCTGGCCCAGCTACAAGACGAATGGAACGGCTACAGCTACGCATAC 1610
   D  I  A  E  G  Q  K  K  I  W  P  S  Y  K  T  N  G  T  A  T  A  T  H  T
ACAGTCGTCCGTGCCGCTGCCTACGGCTACCAGCATGTCCAGTGTTGGTATGGCATAG 1668
   Q  S  S  V  P  L  P  T  A  T  S  M  S  S  V  G  M  A  .
```

Fig. 3

| | | |
|---|---|---|
| A.oryzaeCP1 | 1 | - - - - - M R G Y E F L S V L P L V A A S - - - - - - - - - - - W A L |
| PenicilliumS3 | 1 | - - - - - - - - - - - - - - - - - - - - - - - - - - - - - - - - |
| PenicilliumS1 | 1 | - - - - - - - - - - - - - - - - - - - - - - - - - - - - - - - - |
| A.phoenicis | 1 | - - - - - M R I T S A I A S L L L V G T A T S L Q N - - - P H R R A V |
| A.niger | 1 | M L F R S L L S T A V L A V S L C T D N A S A A K H G R F G Q K A R D |
| | | |
| A.oryzaeCP1 | 20 | P G S T P A S V G R R Q L P K N P T G V K T L T T A N N V T I R Y K E |
| PenicilliumS3 | 1 | - - - - - - - - - - - F V K N - - - - - - - - - - - - - - - - - |
| PenicilliumS1 | 1 | - - - - - - - - - - - - - - - - - S T K N Y R F L N E K T K A N L V |
| A.phoenicis | 28 | P P P L T H R S V A S R A V P V E R R S N D F E Y L T N K T A R F L V |
| A.niger | 36 | A M N I A K R S A N A V K H S L K I P V E D Y Q F L N N K T K P Y R V |
| | | |
| A.oryzaeCP1 | 55 | P G A E G V C E T T P G V K S Y S G Y V D T S P - - E S H T F F W F F |
| PenicilliumS3 | 5 | - - - S G I C E T T P G V N Q Y S G Y L S V G S - - N M N M W F W F F |
| PenicilliumS1 | 18 | H - - H L P D V P Y D I G E M Y S G L M P I D M H N E S R A L F Y I F |
| A.phoenicis | 63 | N G T S I P E V D F D V G E S Y A G L L P N T P T G N S S L F F W F F |
| A.niger | 71 | E - - S L P D V H F D L G E M Y S G L V P I E K G N V S R S L F F V F |
| | | |
| A.oryzaeCP1 | 88 | E A R H N P E T A P I T L W L N G G P G S D S L I G L F E E L G P C H |
| PenicilliumS3 | 35 | E A R N N P Q Q A P L A A W F N G G P G C S S M I G L F Q E N G P C H |
| PenicilliumS1 | 51 | Q P T I G E P V D E V T I W M N G G P G C S S M E S F L Q E T G R F L |
| A.phoenicis | 98 | P S Q N P D A S D E I T I W L N G G P G C S S L D G L L Q E N G P F L |
| A.niger | 104 | Q P T I G E P V D E I T I W L N G G P G C S S L E A F L Q E N G R F V |
| | | |
| A.oryzaeCP1 | 123 | - V N S T F D D Y I N P H S W N E V S N L L F L S Q P L G V G F S Y S |
| PenicilliumS3 | 70 | F V N G D S T P S L N E N S W N N Y A N M I Y I D Q P I G V G F S Y G |
| PenicilliumS1 | 86 | W Q P G T Y A P V E N P Y S W V V L T N V L W V D Q P V G T G Y S I G |
| A.phoenicis | 133 | W Q P G T Y K P V P N P Y S W T N L T N V V Y I D Q P A G T G F S P G |
| A.niger | 139 | W Q P G T Y Q P V E N P Y S W V N L T N V L W V D Q P V G T G F S L G |
| | | |
| A.oryzaeCP1 | 157 | D T V D G S I N P V T G V V E N S S F A G V Q G R Y P T I D A T L I D |
| PenicilliumS3 | 105 | - - T D D V T S T V T - - - - - - - - - - - - - - - - - - - - - - |
| PenicilliumS1 | 121 | T P T A T S Q - - - - - - - - - - - - - - - - - - - - - - - - - |
| A.phoenicis | 168 | P S T V N D E - - - - - - - - - - - - - - - - - - - - - - - - - |
| A.niger | 174 | V P T A T S E - - - - - - - - - - - - - - - - - - - - - - - - - |
| | | |
| A.oryzaeCP1 | 192 | T T N L A A E A A W E I L Q G F L S G L P S L D S R V Q S K D F S L W |
| PenicilliumS3 | 114 | - - - - A A P Y V W N L L Q A F Y A Q R P E Y E S - - - - R D F A I F |
| PenicilliumS1 | 128 | - - - - E E T A Q D F V K F F K N F Q K T Y G I K N - - F K I Y V T |
| A.phoenicis | 175 | - - - - E D V A A Q F N S W F K H F V D T F D L H G - - R K V Y I T |
| A.niger | 181 | - - - - E E I A E D F V K F F K N W Q Q I F G I K N - - F K I Y V T |
| | | |
| A.oryzaeCP1 | 227 | T E S Y G G H Y G P A F F N H F Y E Q N E R I A N G S V N G V Q L N F |
| PenicilliumS3 | 141 | T E S Y G G H Y G P E F A S Y I E Q Q N A A I K A G S V T G Q N V N I |
| PenicilliumS1 | 156 | G E S Y A G R Y V P Y I S A A M L D E K D - K E Y F D L Q G A L A Y D |
| A.phoenicis | 203 | G E S Y A G M Y V P Y I A D A M L N E E D - T T Y F N L K G I Q I N D |
| A.niger | 209 | G E S Y A G R Y V P Y I S A A F L D Q N D - T E H F N L K G A L A Y D |
| | | |
| A.oryzaeCP1 | 262 | N S L G I I N G I I D E A I Q A P Y Y P E - - - - F A V N N T Y G I K |
| PenicilliumS3 | 176 | V A L G V N N G W I D S T I Q E K A Y I D - - - - F S Y N N S Y Q Q I |
| PenicilliumS1 | 190 | P C I G Q F D Y V Q E E I P V V P F V K E N A N L F N F N E T F M A E |
| A.phoenicis | 237 | P S I N S - D S V M M Y S P A V R H L N H Y N N I F R L N S T F L S Y |
| A.niger | 243 | P C I G Q F D Y V Q E E A P V V P F V Q K N N A L F N F N A S F L A E |

Fig. 4A

```
A.oryzaeCP1   293   A V N E T V Y N - - - - Y M K F A N Q M P N G C Q D L I S T C K Q T N
PenicilliumS3 207   I D S S T R D S - - - - L L D A Y N - - - N Q C L P A L Q Q C S Q S G
PenicilliumS1 225   L E H L H K S C G Y A D F I D K Y L T F P P P K E Q P P L F F N Y T S
A.phoenicis   271   I N G K A D K C G Y N A F L D K A I T Y P P P - - - T P F P T A P E I
A.niger       278   L E S I H E Q C G Y K D F I D Q Y L V F P A S G V Q P P K A M N W S D A.oryzaeCP1   324   R T A L A D Y A L C A E A T N M C R D N V E G P Y Y A F A G R G V Y D
PenicilliumS3 235   S T S - - - - - D C T N A D S V C Y Q N I E G P I S S S G D F D V Y D
PenicilliumS1 260   M A N E D V F D M V Y N E V F K I N P C F D L Y E V N L M C P L Q W D
A.phoenicis   303   T E D C Q V W D E V V M A A Y D I N P C F N Y Y H L I D F C P Y L W D
A.niger       313   P T - C D V Y D I V N N A V L D P N P C F N P Y E I N E M C P I L W D A.oryzaeCP1   359   I R - H P Y D D P T P P S Y Y N K F L A K D S V M D A I G V N - I N Y
PenicilliumS3 265   I R - E P S N D P Y P P K T Y S T Y L S D P T V V K A I G A R - T N Y
PenicilliumS1 295   V L A F P T S L V Y Q P A G A T V Y F D R A D V K K A L H A P N V T W
A.phoenicis   338   V L G F P S - - - - L G F G P D N Y F N R S D V Q K I L H V P P T D Y
A.niger       347   V L G F P T E V D Y L P A G A S I Y F D R A D V K R A M H A P N I T W A.oryzaeCP1   392   T Q S N N D V Y Y A F Q Q T G - - - - - D F V W P N F I E D L E E I L
PenicilliumS3 298   Q E C P N G P Y N K F A S T G - - - - - D N P R S - F L S T L S S V V
PenicilliumS1 330   A E C S N N P V F V G G S S G P E Q E G D T S A N P I E H V L P Q V I
A.phoenicis   369   S V C S E T V I F A N G D G S - - - - - D P S S - - - W G P L P S V I
A.niger       382   S E C S V E S V F V G G D G G P E Q E G D Y S A N P I E H V L P Q V I A.oryzaeCP1   422   A L P V R V S L I Y G D A D Y I C N W F G G Q A V S L A A N Y S Q A A
PenicilliumS3 327   Q S G I N V L V W A G D A D W I C N W L G N Y E V A N A V D F P G N A
PenicilliumS1 365   E A T N R V L I S N G D F D M V I L T N G T L L A I Q N M T W N G H L
A.phoenicis   396   E R T N N T I I G H G W L D Y L L F L N G S L A T I Q N M T W N G K Q
A.niger       417   E G T N R V L I G N G D Y D M V I L T N G T L L S I Q N M T W N G K L A.oryzaeCP1   457   Q F R S A G Y T P L K V N G V E Y G E T R E Y G N F S F T R V Y E A G
PenicilliumS3 362   Q F S A L D L A P Y T V N G V E K G Q F K T V D N F S F L K V Y G A G
PenicilliumS1 400   G F Q K K P S A P I D I K I P D L Q Y K E V F A E N - G A S S L D G A
A.phoenicis   431   G F Q S P P V E P L F V P Y H G L A E L Y W G D E P D P Y N L D A G
A.niger       452   G F D T A P S T P I N I D I P D L M Y N E V F I E N - G Y D - P Q G G A.oryzaeCP1   492   H E V P Y Y Q P I A S L Q L F N R T I F G W D I A E G Q K K I W P S Y
PenicilliumS3 397   H E V P Y Y Q P D T A L Q A F K Q I I Q - - - - - - - K K P I S S T -
PenicilliumS1 434   Q G I M G V Q H Y E R G L M K A Q T Y Q S G - - - - H M Q P Q Y Q P -
A.phoenicis   466   A G Y L G T A H T E R G L T F S S V Y L S G - - - - H E I P Q Y V P G
A.niger       485   Q G V M G I Q H Y E R G L M W A E T F Q S G - - - - H M Q P Q F Q P -

A.oryzaeCP1   527   K T N G T A T A T H T Q S S V P L P T A T S M S S V G M A
PenicilliumS3   0   - - - - - - - - - - - - - - - - - - - - - - - - - - - - -
PenicilliumS1 464   - - - - - - R V A Y R H L E W L L K R T D E L Q - - - - -
A.phoenicis   497   A L T A S W S S C L V E L I V F P R R G T T P L N F S - -
A.niger       515   - - - - - - R V S Y R H L E W L L G R R D T L - - - - - -
```

CARBOXYPEPTIDASES AND NUCLEIC ACIDS ENCODING THE SAME

CROSS-REFERENCE TO RELATED APPLICATIONS

This application is a continuation-in-part of pending U.S. application Ser. No. 08/726,880 filed on Oct. 4, 1996, a continuation-in-part of pending U.S. application Ser. No. 08/757,534 filed on Nov. 27, 1996, and a continuation-in-part of PCT/DK97/00230 filed May 20, 1997, which claims priority of Danish application serial no. 0585/96 filed May 20, 1996, which applications are fully incorporated herein by reference.

BACKGROUND OF THE INVENTION

1. Field of the Invention

The present invention relates to polypeptides having carboxypeptidase activity and isolated nucleic acid sequences encoding the polypeptides. The invention also relates to nucleic acid constructs, vectors, and host cells comprising the nucleic acid sequences as well as methods for producing the polypeptides. The present invention further relates to methods of obtaining protein hydrolysates useful as flavor improving agents.

2. Description of the Related Art

Various food products, e.g., soups, sauces and seasonings, contain flavoring agents obtained by hydrolysis of proteinaceous materials. This hydrolysis is conventionally accomplished using strong hydrochloric acid, followed by neutralization with sodium hydroxide. However, such chemical hydrolysis leads to severe degradation of the amino acids obtained during the hydrolysis, and also to hazardous byproducts formed in the course of this chemical reaction. Increasing concern over the use of flavoring agents obtained by chemical hydrolysis has led to the development of erymatic hydrolysis processes.

Enzymatic hydrolysis processes aim at obtaining a high degree of hydrolysis (DH), and this is usually attained using a complex of unspecific acting proteolytic enzymes (i.e., unspecific acting endo- and exo-peptidases). For example, WO 94/25580 describes a method for hydrolyzing proteins by use of an unspecific acting enzyme preparation obtained from *Aspergillus oryzae*. Specific acting proteolytic enzymes have not been used for this purpose because such enzymes only lead to an inadequate degree of hydrolysis.

Acid carboxypeptidases (EC 3.4.16) are serine exopeptidases which catalyze the removal of amino acids from the C-terminus of peptides, oligopeptides or proteins. These carboxypeptidases generally have a narrow substrate specificity, i.e., they can cleave only few amino acids.

Acid carboxypeptidases of *Aspergillus oryzae* have been reported previously. For instance, Nakadai, Nasuno, and Iguchi, 1972, *Agricultural and Biological Chemistry* 36: 1343–1352, disclose a carboxypeptidase I with a molecular weight of 120 kDa (gel filtration) and optimal activity in the pH range 3.0 to 4.0. Nakadai, Nasuno, and Iguchi, 1972, *Agricultural and Biological Chemistry* 36: 1473–1480, disclose a carboxypeptidase II with a molecular weight of 105 kDa (gel filtration) and optimal activity at pH 3.0. Nakadai, Nasuno, and Iguchi, 1972, *Agricultural and Biological Chemistry* 36: 1481–1488, disclose a carboxypeptidase III with a molecular weight of 61 kDa (gel filtration) and a pH optimum of 3.0. Nakadai, Nasuno, and Iguchi, 1972, *Agricultural and Biological Chemistry* 37: 1237–1251, disclose a carboxypeptidase IV with a molecular weight of 43 kDa (gel filtration) and optimal activity at pH 3.0. Tekeuchi and Ichishima, 1986, *Agricultural and Biological Chemistry* 50: 633–638, disclose a carboxypeptidase O with a molecular weight of 73 kDa (SDS-PAGE). Tekeuchi, Ushijima, and Ichishima, 1982, *Current Microbiology* 7: 19–23, disclose a carboxypeptidase O-1 and a carboxypeptidase O-2 both with a molecular weight of 63 kDa (gel filtration) and optimal activity at a pH in the range of 3.7 to 4.0. Ichishima et al., 1972, *Journal of Biochemistry* 72: 1045–1048, disclose a comparison of the enzymatic properties of several Aspergillus acid carboxypeptidases. Azarenkova et al., 1976, *Biokhimiya* 41: 20–27, disclose the isolation of an acid carboxypeptidase from *Aspergillus oryzae* with a molecular weight of 37 kDa (SDS-PAGE) and a pH optimum of 4 to 5.

The production of protein hydrolysates with desirable organoleptic properties and high degrees of hydrolysis generally requires the use of a mixture of peptidase activities. It would be desirable to provide a single component peptidase enzyme which has activity useful for improving the organoleptic properties and degree of hydrolysis of protein hydrolysates used in food products either alone or in combination with other enzymes.

It is an object of the present invention to provide improved polypeptides having carboxypeptidase activity as well as methods of obtaining protein hydrolysates with desirable organoleptic qualities and high degrees of hydrolysis.

SUMMARY OF THE INVENTION

The present invention relates to isolated polypeptides having carboxypeptidase activity selected from the group consisting of:

(a) a polypeptide having an amino acid sequence which has at least 50% identity with the amino acid sequence of SEQ ID NO:2;

(b) a polypeptide encoded by a nucleic acid sequence which hybridizes under medium stringency conditions with (i) the nucleic acid sequence of SEQ ID NO:1, (ii) its complementary strand, or (iii) a subsequence thereof;

(c) a polypeptide having (i) optimal activity in the range of about pH 3.0 to about pH 7.5 at 25° C.; (ii) optimal activity in the range of about 55° C. to about 60° C. at pH 4; (iii) a residual activity of at least about 65.5% after 30 minutes at pH 4.0 and 60° C.; and (iv) a capability to hydrolyze X from N-CBZ-Ala-X wherein N-CBZ is N-carbobenzoxy and X is any amino acid;

(d) an allelic variant of (a) or (b); and (e) a fragment of (a), (b) or (d), wherein the fragment retains carboxypeptidase activity.

The present invention also relates to isolated nucleic acid sequences encoding the polypeptides and to nucleic acid constructs, vectors, and host cells comprising the nucleic acid sequences as well as methods for producing the polypeptides.

The present invention also relates to methods of obtaining hydrolysates from proteinaceous substrates which comprise subjecting the proteinaceous material to a polypeptide with carboxypeptidase activity alone or in combination with an endopeptidase, and to hydrolysates obtained from the method.

The present invention also relates to methods of obtaining from a proteinaceous substrate a hydrolysate enriched in free glutamic acid and/or peptide bound glutamic acid residues, which methods comprise subjecting the substrate to a deamidation process and to the action of a polypeptide having carboxypeptidase activity.

The present invention further relates to flavor-improving compositions comprising a polypeptide with carboxypeptidase activity. The compositions may further comprise additional enzymatic activities.

In a final aspect, the methods of the invention may be used in food related applications to improve flavor, such as baking. Alternatively, flavor improvement in foods may be achieved by the addition of hydrolysates obtained by the methods of the invention.

BRIEF DESCRIPTION OF THE FIGURES

FIG. 3 shows the nucleic acid sequence and the deduced amino acid sequence of the *Aspergillus oryzae* ATCC 20386 carboxypeptidase I (SEQ ID NOS:1 and 2).

FIGS. 4A and 4B show a sequence comparison of the *Aspergillus oryzae* ATCC 20386 carboxypeptidase I to that of other known carboxypeptidases.

DETAILED DESCRIPTION OF THE INVENTION

Polypeptides Having Carboxypeptidase Activity

Figure 1:
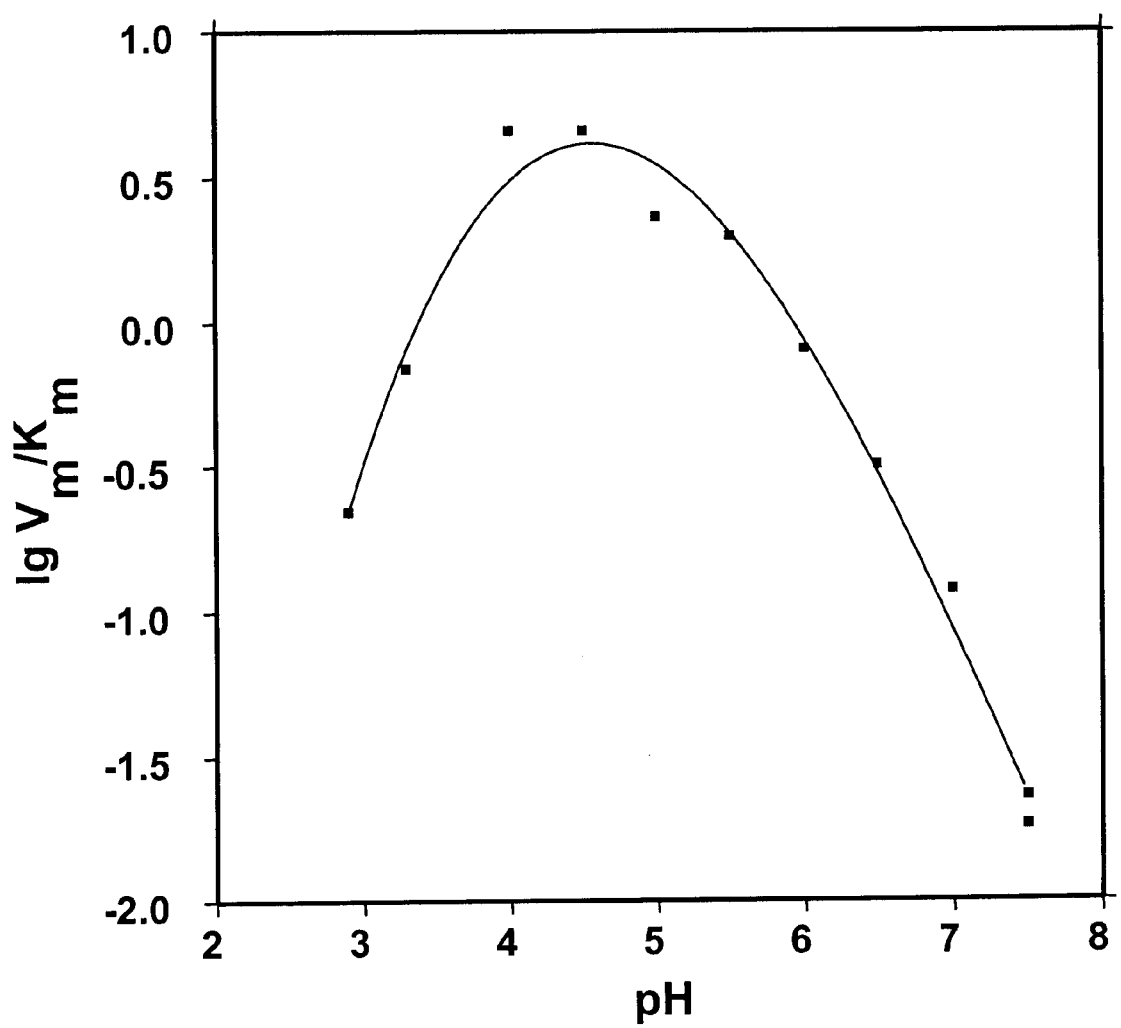
FIG. 1 shows the dependence of *Aspergillus oryzae* ATCC 20386 carboxypeptidase I activity on pH.

The term "carboxypeptidase activity" is defined herein as a peptidase activity which catalyzes the removal of amino acids from the C-terminus of peptides, oligopeptides or proteins. Defined in a general manner, the carboxypeptidase activity is capable of cleaving the amino acid X from the C-terminus of a peptide, polypeptide, or protein, wherein X represents any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val. It will be understood that the isolated polypeptides having carboxypeptidase activity of the present invention are unspecific as to the amino acid sequence of the peptide, polypeptide, or protein to be cleaved.

In a first embodiment, the present invention relates to isolated polypeptides having an amino acid sequence which has a degree of identity to the amino acid sequence of SEQ ID NO:2 of at least about 50%, preferably at least about 60%, preferably at least about 70%, more preferably at least about 80%, even more preferably at least about 90%, most preferably at least about 95%, and even most preferably at least about 97%, which retain carboxypeptidase activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO:2. For purposes of the present invention, the degree of identity between two amino acid sequences is determined by the Clustal method (Higgins, 1989, *CABIOS* 5: 151–153) with an identity table, a gap penalty of 10, and a gap length penalty of 10.

Preferably, the polypeptides of the present invention comprise the amino acid sequence of SEQ ID NO:2 or an allelic variant and a fragment thereof, wherein the fragment retains carboxypeptidase activity. In a more preferred embodiment, the polypeptides of the present invention comprise the amino acid sequence of SEQ ID NO:2. In another preferred embodiment, the polypeptide of the present invention has the amino acid sequence of SEQ ID NO:2 or a fragment thereof, wherein the fragment retains carboxypeptidase activity. In a most preferred embodiment, the polypeptide has the amino acid sequence of SEQ ID NO:2.

Preferably, a fragment contains at least 300 amino acid residues, more preferably at least 400 amino acid residues, and most preferably at least 500 amino acid residues.

An allelic variant denotes any of two or more alternative forms of a gene occupying the same chomosomal locus. Allelic variation arises naturally through mutation, and may result in phenotypic polymorphism within populations. Gene mutations can be silent (no change in the encoded polypeptide) or may encode polypeptides having altered amino acid sequences. The term allelic variant is also used to denote a protein encoded by an allelic variant of a gene.

The amino acid sequences of the homologous polypeptides may differ from the amino acid sequence of SEQ ID NO:2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine and valine), aromatic amino acids (such as phenylalanine, tryptophan and tyrosine), and small amino acids (such as glycine, alanine, serine, threonine and methionine). Amino acid substitutions which do not generally alter the specific activity are known in the art and are described, e.g., by H. Neurath and R. L. Hill, 1979, In, The Proteins, Academic Press, New York. The most commonly occurring exchanges are Ala/Ser, Val/lBe, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Lxu/Val, Ala/Glu, and Asp/Gly as well as these in reverse.

In a second embodiment, the present invention relates to isolated polypeptides having carboxypeptidase activity which are encoded by nucleic acid sequences which hybridize under low stringency conditions, more preferably medium stringency conditions and most preferably high stringency conditions, with an oligonucleotide probe which hybridizes under the same conditions with the nucleic acid sequence of SEQ ID NO:1 or its complementary strand (J. Sambrook, E. F. Fritsch, and T. Maniatus, 1989, *Molecular Cloning, A Laboratory Manual*, 2d edition, Cold Spring Harbor, N.Y.); or allelic variants and fragments of the polypeptides.

Hybridization indicates that the nucleic acid sequence hybridizes to the oligonucleotide probe corresponding to the polypeptide encoding part of the nucleic acid sequence shown in SEQ ID NO:1, under low to high stringency conditions (i.e., prehybridization and hybridization at 42° C. in 5×SSPE, 0.3% SDS, 200 mg/ml sheared and denatured salmon sperm DNA, and either 25, 35 or 50% formamide for low, medium and high stringencies, respectively), following standard Southern blotting procedures.

The amino acid sequence of SEQ ID NO:2 or a partial amino acid sequence thereof may be used to design an oligonucleotide probe, or a nucleic acid sequence encoding a polypeptide of the present invention, such as the nucleic acid sequence of SEQ ID NO:1, or a subsequence thereof, may be used to identify and clone DNA encoding polypeptides having carboxypeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with $^{32}$p, $^{3}$H, $^{35}$S, biotin, or avidin).

Thus, a genomic, cDNA or combinatorial chemical library prepared from such other organisms may be screened for DNA which hybridizes with the probes described above and which encodes a polypeptide having carboxypeptidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO:1, the carrier material is used in a Southern blot in which the carrier material is finally washed three times for 30 minutes each using 2×SSC, 0.2% SDS at a temperature of at least 50° C., more preferably at least 55° C., more preferably at least 60° C., more preferably at least 65° C., even more preferably at least 70° C., and most preferably at least 75° C. Molecules to which the oligonucleotide probe hybridizes under these conditions are detected using X-ray film.

In a third embodiment, the present invention relates to isolated polypeptides having (i) optimal activity in the range of about pH 3.0 to about pH 7.5 at 25° C.; (ii) optimal activity in the range of about 55° C. to about 60° C. at pH 4; (iii) a residual activity of at least about 65.5% after 30 minutes at pH 4.0 and 60° C.; and (iv) a capability to hydrolyze N-CBZ-Ala-X wherein X is any amino acid. Preferably, the polypeptides have optimal activity at a pH in the range of about 4.0 to about 6.0 at 25° C. and most preferably in the range of about 4.0 to about 5.0. The polypeptides also preferably have a molecular weight in the range of about 66 kDa to about 70 kDa by SDS-PAGE. Furthermore, the polypeptides preferably have a residual activity of at least about 60%, most preferably at least 65%, and most preferably a residual activity in the range of 50–85%, after 10 minutes at pH 4.0 and 60° C. The polypeptides of the present invention also preferably have a residual activity of at least about 70%, most preferably at least 75%, and most preferably a residual activity in the range of 65–90%, after 30 minutes at pH 4.0 and 55° C. Preferably, the polypeptides are capable of hydrolyzing N-CBZ-Ala-X where X is Ile, Glu, Lys, Arg, Asp, Asn, Phe, or Tyr.

In a fourth embodiment, the present invention relates to isolated polypeptides having immunochemical identity or partial iimunochemical identity to the polypeptide having the amino acid sequence of SEQ ID NO:2. The immunochemical properties are determined by immunological cross-reaction identity tests by the well-known Ouchterlony double immunodiffusion procedure. Specifically, an antiserum containing antibodies which are immunoreactive or bind to epitopes of the polypeptide having the amino acid sequence of SEQ ID NO:2 are prepared by immunizing rabbits (or other rodents) according to the procedure described by Harboe and Ingild, In N. H. Axelsen, J. Krøll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27–31). A polypeptide having immunochemical identity is a polypeptide which reacts with the antiserum in an identical fashion such as total fusion of precipitates, identical precipitate morphology, and/or identical electrophoretic mobility using a specific immunochemical technique. A further explanation of immunochemical identity is described by Axelsen, Bock, and Kroll, In N. H. Axelsen, J. Krøøll, and B. Weeks, editors, *A Manual of Quantitative Immunoelectrophoresis*, Blackwell Scientific Publications, 1973, Chapter 10. A polypeptide having partial immunochemical identity is a polypeptide which reacts with the antiserum in a partially identical fashion such as partial fusion of precipitates, partially identical precipitate morphology, and/or partially identical electrophoretic mobility using a specific immunochemical technique. A further explanation of partial immunochemical identity is described by Bock and Axelsen, In N. H. Axelsen, J. Krøll, and B. Weeks, editors, *A Manual of Quantitative Immunoelectrophoresis*, Blackwell Scientific Publications, 1973, Chapter 11.

Polypeptides encoded by nucleic acid sequences which hybridize with an oligonucleotide probe which hybridizes with the nucleic acid sequence of SEQ ID NO:1 or its complementary strand, or allelic variants and fragments of the polypeptides, the homologous polypeptides and polypeptides having identical or partially identical immunological properties may be obtained from microorganisms of any genus.

In a preferred embodiment, these polypeptides are obtained from a bacterial source. For example, these polypeptides may be obtained from a gram positive bacterium such as a Bacillus strain, e.g., *Bacillus alkalophilus, Bacillus anyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a Streptomyces strain, e.g., *Streptomyces lividans* or *Streptomyces murinus*, or from a gram negative bacterium, e.g., *E. coli* or Pseudomonas sp.

In another preferred embodiment, these polypeptides are obtained from a fungal source. For example, the polypeptides may be obtained from a yeast strain, e.g., a Candida, Kluyveromyces, Pichia, Saccharomyces, Schizosaccharomyces, or Yarrowia strain. In a preferred embodiment, the polypeptides are obtained from a *Saccharomyces carlsbergensis, Saccharomyces cerevisiae, Saccharomyces diastaicus, Saccharomyces douglasii, Saccharomyces kluyveri, Saccharomyces norbensis* or *Saccharomyces oviformis* strain. The polypeptides may also be obtained from a filamentous fungal strain. For example, the polypeptides may be obtained from an Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, or Trichoderma strain. In a most preferred embodiment, the polypeptides are obtained from an *Aspergillus aculeatus, Aspergillus awamori, Aspergillus foetdus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides, Fusarium venenatum, Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* strain.

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

The polypeptides of the present invention are preferably obtained from species of Aspergillus including, but not limited to, *Aspergillus aculeatus, Aspergillus awamori, Aspergillus foetidus, Aspergillus japonicus, Aspergillus nidulans, Aspergillus niger,* or *Aspergillus oryzae*. Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

In a more preferred embodiment, a polypeptide of the present invention is obtained from an *Aspergillus oryzae* strain, and most preferably from *Aspergillus oryzae* ATCC 20386 or a mutant strain thereof, e.g., the polypeptide with the amino acid sequence of SEQ ID NO:2.

The polypeptides of the present invention may also be obtained from microorganisms which are synonyms of Aspergillus as defined by Raper, K. D. and Fennel, D. I., 1965, *The Genus Aspergillus*, The Wilkins Company, Baltimore. Aspergilli are mitosporic fungi characterized by an aspergillum conprised of a conidiospore stipe with no known teleomorphic states terminating in a vesicle, which in turn bears one or two layers of synchronously formed specialized cells, variously referred to as sterigmata or phialides, and asexually formed spores referred to as conidia. Known teleomorphs of Aspergillus include Eurotium, Neosartorya, and Emericella. Strains of Aspergillus and teleomorphs thereof are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

For purposes of the present invention, the term "obtained from" as used herein in connection with a given source shall mean that the polypeptide is produced by the source or by a cell in which a gene from the source has been inserted.

As defined herein, an "isolated" polypeptide is a polypeptide which is essentially free of other non-carboxypeptidase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Nucleic Acid Sequences

The present invention also relates to isolated nucleic acid sequences which encode a polypeptide of the present invention. In a preferred embodiment, the nucleic acid sequence encodes a polypeptide obtained from Aspergillus, e.g., *Aspergillus oryzae*, and in a more preferred embodiment, the nucleic acid sequence is obtained from *Aspergillus oryzae* ATCC 20386, e.g., the nucleic acid sequence of SEQ ID NO:1. In another more preferred embodiment, the nucleic acid sequence is the sequence contained in plasmid pEJG12 which is contained in *Escherichia coli* NRRL B-21616. The present invention also encompasses nucleic acid sequences which encode a polypeptide having the amino acid sequence of SEQ ID NO:2, which differ from SEQ ID NO:1 by virtue of the degeneracy of the genetic code.

The present invention also relates to subsequences of SEQ ID NO:1 which encode fragments of SEQ ID NO:2 which retain carboxypeptidase activity. Preferably, a subsequence contains at least 900 nucleotides, more preferably at least 1200 nucleotides, and most preferably at least 1500 nucleotides.

As described above, the nucleic acid sequences may be obtained from microorganisms which are synonyms or teleomorphs of *Aspergillus oryzae* as defined by Raper, K. D. and Fennel, D. I., 1965, supra.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Aspergillus, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to the nucleic acid sequence of SEQ ID NO:1 of at least about 50%, preferably about 60%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the Clustal method (Higgins, 1989, supra) with an identity table, a gap penalty of 10, and a gap length penalty of 10.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of SEQ ID NO:1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al, 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scarning mutagenesis (see, e.g., Cunningham and Wells, 1989, *Science* 244: 1081–1085). In the latter technique mutations are introduced at every positively charged residue in the molecule, and the resultant mutant molecules are tested for carboxypeptidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al, 1992, *Science* 255: 306–312; Smith et al, 1992, *Journal of Molecular Biology* 224: 899–904; Wlodaver et al, 1992, *FEBS Letters* 309: 59–64).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include, ligating the coding sequences encoding the polypeptides so that they are in frame and that expression of the fused polypeptide is under control of the same promoter(s) and terminator.

The present invention also relates to isolated nucleic acid sequences encoding a polypeptide of the present invention, which hybridize under low stringency conditions, more preferably medium stringency conditions and most preferably high stringency conditions, with an oligonucleotide probe which hybridizes under the same conditions with the nucleic acid sequence of SEQ ID NO:1 or its complementary strand; or allelic variants and subsequences thereof (Sambrook et al., 1989, supra).

Nucleic Acid Constructs

The present invention also relates to nucleic acid constructs comprising a nucleic acid sequence of the present invention operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defmed herein as a nucleic acid molecule, either single-or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" as defined herein is a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence encoding a polypeptide prior to its insertion into a vector may be desirable or necessary depending on the expression vector. The techniques for modifying nucleic acid sequences utilizing cloning methods are well known in the art.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defmed herein as a configuration in which a control sequence is appropriately placed at a position relative to the coding sequence of the DNA sequence such that the control sequence directs the production of a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptonzyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (Villa-Kamaroff et al., 1978, *Proceedings of the National Academy of Sciences USA* 75: 3727–3731), as well as the tac promoter (DeBoer et al, 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusafium oxysporum* trypsin-like protease (as described in U.S. Pat. No. 4,288,627, which is incorporated herein by reference), and mutant, truncated, and hybrid promoters thereof. Particularly preferred promoters for use in filamentous fungal host cells are the TAKA amylase, NA2-tpi (a hybrid of the promoters from the genes encoding *Aspergillus niger* neutral a-amylase and *Aspergillus oryzae* triose phosphate isomerase), and glaA promoters.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423–488. In a mammalian host cell, useful promoters include viral promoters such as those from Simian Virus 40 (SV40), Rous sarcoma virus (RSV), adenovirus, and bovine papilloma virus (BPV).

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is finctional in the host cell of choice may be used in the present invention.

Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes encoding *Saccharomyces cerevisiae* enolase, *Saccharomyces cerevisiae* cytochrome C (CYC1), or *Saccharomyces cerevisiae* glyceraldehyde-3-phosphate dehydrogenase. Other useful terminators for yeast host cells are described by Romanos et al., 1992, supra. Terminator sequences are well known in the art for mammalian host cells.

The control sequence may also be a suitable leader sequence, a nontranslated region of a MRNA which is important for translation by the host cell. The leader sequence is operably linked to the 5' terminus of the nucleic acid sequence encoding the polypeptide. Any leader sequence which is functional in the host cell of choice may be used in the present invention.

Preferred leaders for filamentous fungal host cells are obtained from the genes encoding *Aspergillus oryzae* TAKA amylase and *Aspergillus oryzae* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenaselglyceraldehyde-3-phosphate dehydrogenase genes (ADH2/GAP).

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

Useful polyadenylation sequences for yeast host cells are described by Guo and Sherman, 1995, *Molecular Cellular Biology* 15: 5983–5990. Polyadenylation sequences are well known in the art for mammalian host cells.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. The signal peptide coding region may be obtained from a glucoamylase or an amylase gene from an Aspergillus species, a lipase or proteinase gene from a Rhizomucor species, the gene for the alpha-factor from *Saccharomyces cerevisiae*, an amylase or a protease gene from a Bacillus species, or the calf preprochymosin gene. However, any signal peptide coding region which directs the expressed polypeptide into the secretory pathway of a host cell of choice may be used in the present invention.

An effective signal peptide coding region for bacterial host cells is the signal peptide coding region obtained from the maltogenic amylase gene from Bacillus NCIB 11837, the *Bacillus stearothennophilus* alpha-amylase gene, the *Bacillus licheniformis* subtilisin gene, the Bacillus licheniformis beta-lactamase gene, the *Bacillus stearothennophilus* neutral proteases genes (nprT, nprS, nprM), and the *Bacillus subtilis* PrsA gene. Further signal peptides are described by Simonen and Palva, 1993, *Microbiological Reviews* 57: 109–137.

An effective signal peptide coding region for filamentous fungal host cells is the signal peptide coding region obtained from *Aspergillus oryzae* TAKA amylase gene, *Aspergillus niger* neutral amylase gene, the *Rhizomucor miehei* aspartic proteinase gene, the *Humicola lanuginosa* cellulase gene, or the *Rhizomucor miehei* lipase gene.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the ammo terminus of a polypeptide. The resultant polypeptide is known as a proenzyme or propolypeptide (or a zymogen in some cases). A propolypeptide is generally inactive and can be converted to mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, or the *Myceliophthora thermophila* laccase gene (WO 95133836).

The nucleic acid constructs of the present invention may also comprise one or more nucleic acid sequences which encode one or more factors that are advantageous for directing the expression of the polypeptide, e.g., an activator (e.g., a trans-acting factor), a chaperone, and a processing protease. Any factor that is functional in the host cell of choice may be used in the present invention. The nucleic acids encoding one or more of these factors are not necessarily in tandem with the nucleic acid sequence encoding the polypeptide.

An activator is a protein which activates transcription of a nucleic acid sequence encoding a polypeptide (Kudla et al., 1990, *EMBO Journal* 9: 1355–1364; Jarai and Buxton, 1994, *Current Genetics* 26: 2238–244; Verdier, 1990, *Yeast* 6: 271–297). The nucleic acid sequence encoding an activator may be obtained from the genes encoding *Bacillus stearothennophilus* NprA (nprA), *Saccharomyces cerevisiae* heme activator protein 1 (hap1), *Saccharomyces cerevisiae* galactose metabolizing protein 4 (gal4), and *Aspergillus nidulans* ammonia regulation protein (areA). For further examples, see Verdier, 1990, supra and MacKenzie et al, 1993, *Journal of General Microbiology* 139: 2295–2307.

A chaperone is a protein which assists another polypeptide in folding properly (Hartl et al., 1994, *TIBS* 19: 20–25; Bergeron et al., 1994, *TIBS* 19: 124–128; Demolder et al., 1994, *Journal of Biotechnology* 32: 179–189; Craig, 1993, *Science* 260: 1902–1903; Gething and Sambrook, 1992, *Nature* 355: 33–45; Puig and Gilbert, 1994, *Journal of Biological Chemistry* 269: 7764–7771; Wang and Tsou, 1993, *The FASEB Journal* 7: 1515–11157; Robinson et al, 1994, *Bio/Technology* 1: 381–384). The nucleic acid sequence encoding a chaperone may be obtained from the genes encoding *Bacillus subtilis* GroE proteins, *Aspergillus oryzae* protein disulphide isomerase, *Saccharomyces cerevisiae* calnexin, *Saccharomyces cerevisiae* BiP/GRP78, and *Saccharomyces cerevisiae* Hsp70. For further examples, see Gething and Sambrook, 1992, supra, and Hartl et al., 1994, supra.

A processing protease is a protease that cleaves a propeptide to generate a mature biochemically active polypeptide (Enderlin and Ogrydziak, 1994, *Yeast* 10: 67–79; Fuller et al., 1989, *Proceedings of the National Academy of Sciences USA* 86: 1434–1438; Julius et al., 1984, *Cell* 37: 1075–1089; Julius et al., 1983, *Cell* 32: 839–852). The nucleic acid sequence encoding a processing protease may be obtained from the genes encoding *Saccharomyces cerevisiae* dipeptidylaminopeptidase, *Saccharomyces cerevisiae* Kex2, and *Yarrowia lipolytica* dibasic processing endoprotease (xpr6).

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. The vector system may be a single vector or plasmid or two or more vectors or plasmids which together contain the total DNA to be introduced into the genome of the host cell, or a transposon.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. A frequently used mammalian marker is the dihydrofolate reductase gene. Suitable markers for yeast host cells are ADE2, HIS3, LEU2, LYS2, MET3, TRP1, and URA3. A selectable marker for use in a filamentous fungal host cell may be selected from the group including, but not limited to, amidS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), and glufosinate resistance markers, as well as equivalents from other species. Preferred for use in an Aspergillus cell are the amdS and pyrG genes of *Aspergillus nidulans* or *Aspergillus oryzae* and the bar gene of *Streptomyces hrygroscopicus*. Furthermore, selection may be accomplished by co-transformation, e.g., as described in WO 91/17243, where the selectable marker is on a separate vector.

The vectors of the present invention preferably contain an element(s) that permits stable integration of the vector into the host cell genome or autonomous replication of the vector in the cell independent of the genome of the cell.

The vectors of the present invention may be integrated into the host cell genome when introduced into a host cell. For integration, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination. These nucleic acid sequences may be any sequence that is homologous with a target sequence in the genome of the host cell, and, furthermore, may be non-encoding or encoding sequences.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB 110, pE194, pTA1060, and pAMβ1 permitting replication in Bacillus. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence encoding a polypeptide of the present invention may be inserted into the host cell to amplify expression of the nucleic acid sequence. Stable amplification of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by culturing the cells in the presence of the appropriate selectable agent.

The procedures used to ligate the elements described above to construct the recombinant expression vectors of the present invention are well known to one skilled in the art (see, e.g., Sambrook et al, 1989, supra).

Host Cells

The present invention also relates to recombinant host cells, comprising a nucleic acid sequence of the invention, which are advantageously used in the recombinant production of the polypeptides. The term "host cell" encompasses any progeny of a parent cell which is not identical to the parent cell due to mutations that occur during replication.

The cell is preferably transformed with a vector comprising a nucleic acid sequence of the invention followed by integration of the vector into the host chromosome. "Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The choice of a host cell will to a large extent depend upon the gene encoding the polypeptide and its source. The host cell may be a unicellular microorganism, e.g., a prokaryote, or a non-unicellular microorganism, e.g., a eukaryote. Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus coagulans, Bacillus lautus, Bacillus lentus, Bacillus lichenifonnis, Bacillus megaterium, Bacillus stearothennophilus, Bacillus subtilis*, and *Bacillus thuringiensis*; or a Streptonzyces cell, e.g., *Streptonyces lividans* or *Streptonzyces murinus*, or gram negative bacteria such as *E. coli* and Pseudomonas sp. In a preferred embodiment, the bacterial host cell is a *Bacillus lentus, Bacillus licheniformis, Bacillus stearothennophilus* or *Bacillus subtilis* cell. The transformation of a bacterial host cell may, for instance, be effected by protoplast transformation (see, e.g., Chang and Cohen, 1979, *Molecular General Genetics* 168: 111–115), by using competent cells (see, e.g., Young and Spizizin, 1961, *Journal of Bacteriology* 81: 823–829, or Dubnau and Davidoff-Abelson, 1971, *Journal of Molecular Biology* 56: 209–221), by electroporation (see, e.g., Shigekawa and Dower, 1988, *Biotechniques* 6: 742–751), or by conjugation (see, e.g., Koehler and Thorne, 1987, *Journal of Bacteriology* 169: 5771–5278).

The host cell may be a eukaryote, such as a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). Representative groups of Ascomycota include, e.g., Neurospora, Eupenicillium (=Penicillium), Emericella (=Aspergillus), Eurotium (=Aspergillus), and the true yeasts listed below. Examples of Basidiomycota include mushrooms, rusts, and smuts. Representative groups of Chytridiomycota include, e.g., Allomyces, Blastocladiella, Coelomomyces, and aquatic fungi. Representative groups of Oomycota include, e.g., Saprolegniomycetous aquatic fungi (water molds) such as Achtya. Examples of mitosporic fungi include Aspergillus, Penicillium, Candida, and Alternaria. Representative groups of Zygomycota include, e.g., Rhizopus and Mucor.

In a preferred embodiment, the fingal host cell is a yeast cell. "Yeast" as used herein includes ascosporogenous yeast (Endomycetales), basidiosporogenous yeast, and yeast belonging to the Fungi Imperfecti (Blastomycetes). The ascosporogenous yeasts are divided into the families Spermophthoraceae and Saccharomycetaceae. The latter is comprised of four subfamilies, Schizosaccharomycoideae (e.g., genus Schizosaccharonyces), Nadsonioideae, Lipomycoideae, and Saccharomycoideae (e. g., genera Kluyveromyces, Pichia, and Saccharomyces). The basidiosporogenous yeasts include the genera Leucosporidim, Rhodosporidium, Sporidiobolus, Filobasidium, and Filobasidiella. Yeast belonging to the Fungi Imperfecti are divided into two families, Sporobolomycetaceae (e.g., genera Sorobolomyces and Bullera) and Cryptococcaceae (e.g., genus Candida). Since the classification of yeast may change in the future, for the purposes of this invention, yeast shall be defined as described in *Biology and Activities of Yeast* (Skinner, F. A., Passmore, S. M., and Davenport, R. R., eds, Soc. App. Bacteriol. Symposium Series No. 9, 1980. The biology of yeast and manipulation of yeast genetics are well known in the art (see, e.g., *Biochemistry and Genetics of Yeast*, Bacil, M., Horecker, B. J., and Stopani, A. O. M., editors, 2nd edition, 1987; *The Yeasts*, Rose, A. H., and Harrison, J. S., editors, 2nd edition, 1987; and *The Molecular Biology of the Yeast Saccharomnyces*, Strathem et al., editors, 1981).

In a more preferred embodiment, the yeast host cell is a cell of a species of Candida, Kluyveromyces, Pichia, Saccharomyces, Schizosaccharomyces, or Yarrowia.

In a most preferred embodiment, the yeast host cell is a *Saccharomyces carlsbergensis, Saccharomyces cerevisiae, Saccharomnyces diastaticus, Saccharomyces douglasii, Saccharomnyces kluyveri, Saccharomyces norbensis* or *Saccharomyces ovifornis* cell. In another most preferred embodiment, the yeast host cell is a *Kluyveromyces lactis* cell. In another most preferred embodiment, the yeast host cell is a *Yarrowia lipolytica* cell.

In a preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative. In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, and Trichoderma.

In an even more preferred embodiment, the filamentous fungal host cell is an Aspergillus cell. In another even more preferred embodiment, the filamentous fungal host cell is an Acremonium cell. In another even more preferred embodiment, the filamentous fungal host cell is a Fusarium cell. In another even more preferred embodiment, the filamentous fungal host cell is a Humicola cell. In another even more preferred embodiment, the filamentous fungal host cell is a Mucor cell. In another even more pre ferred embodiment, the filamentous fungal host cell is a Myceliophthora cell. In another even more preferred embodiment, the f ilamentous fungal host cell is a Neutospora cell. In another even more preferred embodiment, the filamentous fungal host cell is a Penicillium cell. In another even more preferred embodiment, the filamentous fungal host cell is a Thielavia cell. In another even more preferred embodiment, the filamentous fungal host cell is a Tolypociadium cell. In another even more preferred embodiment, the filamentous fungal host cell is a Trichoderma cell.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatlm, Fusarium roseum, Fusarium sambucinum, Fusarium sarcochroum, Fusarium sulphureum, Fusarium toruloseum, Fusarium trichothecioides*, or *Fusarium venenatum* cell. In an even most preferred embodiment, the filamentous fungal parent cell is a *Fusarium venenatum* (Nirenberg sp. nov.). In another most preferred embodiment, the filamentous fungal host cell is a *Humicola insolens* or *Humicola lanuginosa* cell. In another most preferred embodiment, the filamentous fingal host cell is a *Mucor miehei* cell. In another most preferred embodiment, the filamentous fungal host cell is a *Myceliophthora thernophilum* cell. In another most preferred embodiment, the filamentous fungal host cell is a *Neurospora crassa* cell. In another most preferred embodiment, the filamentous fungal host cell is a *Penicillium purpurogenum* cell. In another most preferred embodiment, the filamentous fungal host cell is a *Thielavia terrestris* cell. In another most preferred embodiment, the Trichoderma cell is a *Trichoderma harzianum, Trichoderma koningii, Trichoderma longibrachiatum, Trichoderna reesei* or *Trichoderma viride* cell.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 147–1474. A suitable method of transforming Fusanium species is described by Malardier et al., 1989, *Gene* 78:

147–156 or in WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920. Mammalian cells may be transformed by direct uptake using the calcium phosphate precipitation method of Graham and Van der Eb (1978, Virology 52: 546).

Methods of Production

The present invention also relates to methods for producing a polypeptide of the present invention comprising (a) cultivating a strain, which in its wild-type form is capable of producing the polypeptide, to produce a supernatant comprising the polypeptide; and (b) recovering the polypeptide. Preferably, the strain is of the genus Aspergillus.

The present invention also relates to methods for producing a polypeptide of the present invention comprising (a) cultivating a host cell under conditions conducive for production of the polypeptide; and (b) recovering the polypeptide.

In both methods, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art (see, e.g., references for bacteria and yeast; Bennett, J. W. and LaSure, L., editors, *More Gene Manipulations in Fungi*, Academic Press, CA, 1991). Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it is recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide. Procedures for determining carboxypeptidase activity are known in the art and include, e.g., o-phthaldialdehyde together with dithiothreitol to monitor the liberation of free amino acids under enzymatic hydrolysis according to the procedure of Roth, 1971, *Analytical Chemistry* 43: 880.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Removal or Reduction of Carboxypeptidase Activity

The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell.

The construction of strains which have reduced carboxypeptidase activity may be conveniently accomplished by modification or inactivation of a nucleic acid sequence necessary for expression of the polypeptide having carboxypeptidase activity in the cell. The nucleic acid sequence to be modified or inactivated may be, for example, a nucleic acid sequence encoding the polypeptide or a part thereof essential for exhibiting carboxypeptidase activity, or the nucleic acid sequence may have a regulatory function required for the expression of the polypeptide from the coding sequence of the nucleic acid sequence. An example of such a regulatory or control sequence may be a promoter sequence or a functional part thereof, i.e., a part which is sufficient for affecting expression of the polypeptide. Other control sequences for possible modification are described above.

Modification or inactivation of the nucleic acid sequence may be performed by subjecting the cell to mutagenesis and selecting for cells in which the carboxypeptidase producing capability has been reduced. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the cell to be mutagenized in the presence of the mutagenizing agent of choice under suitable conditions, and selecting for cells exhibiting reduced carboxypeptidase activity or production.

Modification or inactivation of production of a polypeptide of the present invention may be accomplished by introduction, substitution or removal of one or more nucleotides in the nucleic acid sequence encoding the polypeptide or a regulatory element required for the transcription or translation thereof. For example, nucleotides may be inserted or removed so as to result in the introduction of a stop codon, the removal of the start codon, or a change of the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleic acid sequence to be modified, it is preferred that the modification be performed in vitro as exemplified below.

An example of a convenient way to inactivate or reduce production by a host cell of choice is based on techniques of gene replacement or gene interruption. For example, in the gene interruption method, a nucleic acid sequence corresponding to the endogenous gene or gene fragment of interest is mutagenized in vitro to produce a defective nucleic acid sequence which is then transformed into the host cell to produce a defective gene. By homologous recombination, the defective nucleic acid sequence replaces the endogenous gene or gene fragment. It may be desirable that the defective gene or gene fragment also encodes a marker which may be used for selection of transformants in which the gene encoding the polypeptide has been modified or destroyed.

Alternatively, modification or inactivation of the nucleic acid sequence encoding a polypeptide of the present invention may be performed by established anti-sense techniques using a nucleotide sequence complementary to the polypeptide encoding sequence. More specifically, production of the polypeptide by a cell may be reduced or eliminated by introducing a nucleotide sequence complementary to the nucleic acid sequence encoding the polypeptide which may be transcribed in the cell and is capable of hybridizing to the polypeptide mRNA produced in the cell. Under conditions allowing the complementary anti-sense nucleotide sequence to hybridize to the polypeptide mRNA, the amount of polypeptide translated is thus reduced or eliminated.

It is preferred that the cell to be modified in accordance with the methods of the present invention is of microbial origin, for example, a fungal strain which is suitable for the production of desired protein products, either homologous or heterologous to the cell.

The present invention further relates to a mutant cell of a parent cell which comprises a disruption or deletion of a nucleic acid sequence encoding the polypeptide or a control sequence thereof, which results in the mutant cell producing less of the polypeptide than the parent cell.

The polypeptide-deficient mutant cells so created are particularly useful as host cells for the expression of homologous and/or heterologous polypeptides. Therefore, the present invention further relates to methods for producing a homologous or heterologous polypeptide comprising (a) culturing the mutant cell under conditions conducive for production of the polypeptide; and (b) recovering the polypeptide. In the present context, the term "heterologous polypeptides" is defined herein as polypeptides which are not native to the host cell, a native protein in which modifications have been made to alter the native sequence, or a native protein whose expression is quantitatively altered as a result of a manipulation of the host cell by recombinant DNA techniques.

In a still further aspect, the present invention relates to a method for producing a protein product essentially free of carboxypeptidase activity by fermentation of a cell which produces both a polypeptide of the present invention as well as the protein product of interest. The method comprises adding an effective amount of an agent capable of inhibiting carboxypeptidase activity to the fermentation broth either during or after the fermentation has been completed, recovering the product of interest from the fermentation broth, and optionally subjecting the recovered product to further purification. This method is further illustrated in the examples below.

In a still further alternative aspect, the present invention relates to a method for producing a protein product essentially free of carboxypeptidase activity, wherein the protein product of interest is encoded by a DNA sequence present in a cell encoding a polypeptide of the present invention. The method comprises cultivating the cell under conditions permitting the expression of the product, subjecting the resultant culture broth to a combined pH and temperature treatment so as to reduce the carboxypeptidase activity substantially, and recovering the product from the culture broth. Alternatively, the combined pH and temperature treatment may be performed on an enzyme preparation recovered from the culture broth. The combined pH and temperature treatment may optionally be used in combination with a treatment with a carboxypeptidase inhibitor.

In accordance with this aspect of the invention, it is possible to remove at least 60%, preferably at least 75%, more preferably at least 85%, still more preferably at least 95%, and most preferably at least 99% of the carboxypeptidase activity. It is contemplated that a complete removal of carboxypeptidase activity may be obtained by use of this method.

The combined pH and temperature treatment is preferably carried out at a pH in the range of 6.5–7 and a temperature in the range of 25–40° C. for a sufficient period of time to attain the desired effect, where typically, 30 to 60 minutes is sufficient.

The methods used for cultivation and purification of the product of interest may be performed by methods known in the art.

The methods of the present invention for producing an essentially carboxypeptidase-free product is of particular interest in the production of eukaryotic polypeptides, in particular fungal proteins such as enzymes. The enzyme may be selected from, e.g., an amylolytic enzyme, a lipolytic enzyme, a proteolytic enzyme, a cellulytic enzyme, an oxidoreductase or a plant cell-wall degrading enzyme. Examples of such enzymes include an aminopeptidase, an amylase, an amyloglucosidase, a carbohydrase, a carboxypeptidase, a catalase, a cellulase, a chitinase, a cutinase, a cyclodextrin glycosyltransferase, a deoxyribonuclease, an esterase, a galactosidase, a beta-galactosidase, a glucoamylase, a glucose oxidase, a glucosidase, a haloperoxidase, a hemicellulase, an invertase, an isomerase, a laccase, a ligase, a lipase, a lyase, a mannosidase, an oxidase, a pectinolytic enzyme, a peroxidase, a phytase, a phenoloxidase, a polyphenoloxidase, a proteolytic enzyme, a ribonuclease, a transferase, a transglutaminase, or a xylanase. The carboxypeptidase-deficient cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

In a further aspect, the present invention relates to a protein product essentially free from carboxypeptidase activity which is produced by a method of the present invention.

Methods of Producing Protein Hydrolysates

The polypeptides of the present invention may be used in the production of protein hydrolysates for enhancing the degree of hydrolysis and flavor development.

The present invention further relates to methods for the use of a polypeptide of the present invention in combination with an endopeptidase to produce a high degree of hydrolysis of a protein-rich material. The method comprises treatment of a proteinaceous substrate with the polypeptide and an endopeptidase. The substrate may be treated with the enzymes concurrently or consecutively.

A polypeptide of the present invention is added to the proteinaceous substrate in an effective amount conventionally employed in protein hydrolysis processes, preferably in the range of from about 0.1 to about 100,000 CPDU per 100 g of protein, and more preferably in the range of from about 1 to about 10,000 CPDU per 100 g of protein. As defined herein, one CPDU (carboxypeptidase unit) is the amount of carboxypeptidase which liberates 1 micromole of glutamate per minute from a 0.5 mM N-CBZ-Ala-Glu (Sigma Chemical Co., St. Louis Mo.) solution at pH 4.5 and 25° C.

The endopeptidase may be obtained from a strain of Bacillus, preferably *Bacillus licheniformis* or *Bacillus subtilis*, a strain of Staphylococcus, preferably *Staphylococcus aureus*, a strain of Streptomyces, preferably *Streptomyces thermovularis* or *Streptozyces griseus*, a strain of Actinomyces species, a strain of Aspergillus, preferably *Aspergillus aculeatus, Aspergillus awamori, Aspergillus foetidus, Aspergillus nidulans, Aspergillus niger*, or *Aspergillus oryzae*, or a strain of Fusarium, preferably *Fusarium venenatum*.

The endopeptidase is added to the proteinaceous substrate in an effective amount conventionally employed in protein hydrolysis processes, preferably in the range of from about 0.05 to about 15 AU/100 g of protein, and more preferably from about 0.1 to about 8 AU/100 g of protein. One AU (Anson Unit) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milli-equivalent of tyrosine. The analytical method AF 4/5 is available upon request from Novo Nordisk A/S, Denmark, which is incorporated herein by reference.

The enzymatic treatment, i.e., the incubation of the substrate with the enzyme preparations, may take place at any convenient temperature at which the enzyme preparation does not become inactivated, preferably in the range of from about 20° C. to about 70° C. In accordance with established practice, the enzyme preparations may be suitably inactivated by increasing the temperature of the incubation mixture to a temperature where the enzymes become inactivated, e.g., to above about 70° C., or similarly by decreasing the pH of the incubation mixture to a point where the enzymes become inactivated, e.g., below about 4.0.

Furthermore, the methods of the present invention result in enhancement of the degree of hydrolysis of a proteinaceous substrate. As used herein, the degree of hydrolysis (DH) is the percentage of the total number of amino bonds in a protein that has been hydrolyzed by a proteolytic enzyme.

In another aspect of the present invention, the hydrolysates have an increased content of Leu, Gly, Ala, and/or Pro, e.g., 1.1 times greater.

The present invention also relates to methods of obtaining a hydrolysate enriched in free glutamic acid and/or peptide bound glutamic acid residues, which method comprises:
 (a) subjecting the substrate to a deamidation process; and
 (b) subjecting the substrate to the action of a polypeptide having carboxypeptidase activity.

The two steps may be performed simultaneously, or the second step may be performed subsequent to the first step.

These methods of the present invention produce protein hydrolysates of excellent flavor because glutamic acid (Glu), whether free or peptide bound, plays an important role in the flavor and palatability of protein hydrolysates. These method also produce protein hydrolysates having improved functionality, in particular, improved solubility, improved emulsifying properties, increased degree of hydrolysis, and improved foaming properties.

The conversion of amides (glutanine or asparagine) into charged acids (glutamic acid or aspartic acid) via the liberation of ammonia is known as deamidation. Deamidation may take place as a non-enzymatic or as an enzymatic deamidation process.

In a preferred embodiment, the deamidation is carried out as an enzymatic deamidation process, e.g., by subjecting the substrate to a transglutaminase and/or peptidoglutaminase.

The transglutaminase may be of any convenient source including mammals, see e.g., JP 1050382 and JP 5023182, including activated Factor XIII, see e.g., WO 93/15234; those derived from fish, see e.g., EP 555,649; and those obtained from microorganisms, see e.g., EP 379,606, WO 96/06931 and WO 96122366. In a preferred embodiment, the transglutaminase is obtained from an Oomycete, including a strain of Phytophthora, preferably *Phytophthora cactorum*, or a strain of Pythium, preferably *Pythium irregulare*, Pythium sp., *Pythium internedium, Pythium ultimun*, or *Pythium periilum* (or *Pythium peniplocum*). In another preferred embodiment, the transglutaminase is of bacterial origin and is obtained from a strain of Bacillus, preferably *Bacillus subtilis*, a strain of Streptoverticillium, preferably *Streptoverticillium mobaraensis, Streptoverticillium griseocarneum*, or *Streptoverticillium cinnamoneum*, and a strain of Streptomyces, preferably *Streptomyces lydicus*.

The peptidoglutaminase may be a peptidoglutamase I (peptidyl-glutaminase; EC 3.5.1.43), or a peptidoglutaminase II protein-glutamine glutaminase; EC 3.5.1.44), or any mixture thereof. The peptidoglutaminase may be obtained from a strain of Aspergillus, preferably *Aspergillus japonicus*, a strain of Bacillus, preferably *Bacillus circulans*, a strain of Cryptococcus, preferably *Cryptococcus albidus*, or a strain of Debaryonlyces, preferably *Debaryomyces kloechen*.

The transglutaminase is added to the proteinaceous substrate in an effective amount conventionally employed in deamidation processes, preferably in the range of from about 0.01 to about 5% (w/w), and more preferably in the range of from about 0.1 to about 1% (w/w) of enzyme preparation relating to the amount of substrate.

The peptidoglutaminase is added to the proteinaceous substrate in an effective amount conventionally employed in deamidation processes, preferably in the range of from about 0.01 to about 100,000 PGase Units per 100 g of substrate, and more preferably in the range of from about 0.1 to about 10,000 PGase Units per 100 g of substrate.

The peptidoglutamnase activity may be determined according to the procedure of Cedrangoro et al. (1965, *Enzymologia* 29: 143). According to this procedure, 0.5 ml of an enzyme sample, adjusted to pH 6.5 with 1 N NaOH, is charged into a small vessel. Then 1 ml of a borate pH 10.8 buffer solution is added to the vessel. The discharged ammonia is absorbed by 5 N sulphuric acid, and by use of Nessler's reagent the mixture is allowed to form color which is measured at 420 nm. One PGase unit is the amount of enzyme capable of producing 1 micromole of ammonia per minute under these conditions.

Alternatively, the peptidoglutaminase activity may be determined according to the procedure described in U.S. Pat. No. 3,857,967 or Example 11 below.

In step (b) of the methods of the present invention, the substrate is subjected to a polypeptide of the present invention. A polypeptide of the present invention is added to the proteinaceous substrate in an effective amount conventionally employed in protein hydrolysis processes, preferably in the range of from about 0.001 to about 0.5 AU/100 g of substrate, more preferably in the range of from about 0.01 to about 0.1 AU/100 g of substrate.

In another embodiment, the methods of the present invention for producing a hydrolysate enriched in free glutamic acid and/or peptide bound glutamic acid residues fer comprise:

(c) subjecting the substrate to one or more unspecific acting endo- and/or exopeptidase enzymes.

This step may take place simultaneously with steps (a) and (b), or may follow steps (a) and (b).

In a preferred embodiment, the unspecific acting endo- and/or exo-peptidase enzyme is obtained from a strain of Aspergillus, preferably *Aspergillus niger, Aspergillus oryzae*, or *Aspergillus sojae*, or a strain of Bacillus, preferably *Bacillus amyloliqueaciens, Bacillus lentus, Bacillus licheniformis*, or *Bacillus subtilis*.

The unspecific acting endo- and/or exo-peptidase enzyme is added to the substrate in an effective amount conventionally employed in protein hydrolysis processes, preferably in the range of from about 0.05 to about 15 CPU/100 g of substrate, and more preferably in the range of from about 0.1 to about 5 CPU/100 g of substrate. One CPU (Casein Protease Unit) is defined as the amount of enzyme liberating 1 micromole of primary amino groups (determined by comparison with a serine standard) per minute from casein under standard conditions, i.e., incubation for 30 minutes at 25° C. and pH 9.5. The analytical method AF 228/1, which is incorporated herein by reference, is available upon request from Novo Nordisk A/S, Bagsvarrd, Denmark.

Each enzymatic treatment may take place at any temperature at which the enzyme preparation does not become inactivated, preferably in the range of from about 20° C. to about 70° C. The enzyme preparation may then be inactivated by increasing the temperature, e.g., to above about 70° C., or by decreasing the pH, e.g., below about 4.0.

The proteinaceous substrate used in the methods of the present invention may consist of intact proteins, prehydrolyzed proteins (i.e., peptides), or a mixture thereof. The proteinaceous substrate may be of vegetable or animal origin. Preferably, the proteinaceous substrate is of vegetable origin, e.g., soy protein, grain protein, e.g., wheat gluten, corn gluten, barley, rye, oat, rice, zein, lupine, cotton seed protein, rape seed protein, peanut, alfalfa protein, pea protein, fabaceous bean protein, sesame seed protein, or sunflower. A proteinaceous substrate of animal origin may be whey protein, casein, meat proteins, fish protein, red blood cells, egg white, gelatin, or lactoalbumin.

The present invention also relates to protein hydrolysates produced by these methods.

Other Uses

The present invention also relates to methods of deactivating enzymes with a polypeptide of the present invention.

Furthermore, a polypeptide of the present invention may be useful for a number of purposes in which a specific cleavage of peptide sequences is desirable. For instance, some proteins or peptides are synthesized in the form of inactive precursors comprising a number of additional amino acid residues at the N-terrinai of the mature protein. A polypeptide of the present invention could provide the necessary post-translational processing to activate such precursor proteins.

Polypeptide Compositions

In a still further aspect, the present invention relates to polypeptide compositions comprising a polypeptide of the present invention. Preferably, the compositions are enriched in a polypeptide of the present invention. In the present context, the term "enriched" indicates that the carboxypeptidase activity of the polypeptide composition has been increased, e.g., with an enrichment factor of 1.1.

The polypeptide composition may comprise a polypeptide of the invention as the major enzymatic component, e.g., a mono-component polypeptide composition. Alternatively, the composition may comprise multiple enzymatic activities, such as an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, or a xylanase. The additional enzyme(s) may be producible by means of a microorganism belonging to the genus Aspergillus, preferably *Aspergillus aculeatus, Aspergillus awamori, Aspergillus niger*, or *Aspergillus oryzae*, or Trichoderma, Humicola, preferably *Humicola insolens*, or Fusarium, preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium renculatum, Fusarium roseum, Fusarium sambucinum, Fusarium sarcochroum, Fusarium sulphureum, Fusarium toruloseum, Fusarium trichothecioides*, or *Fusarium venenatum*.

In a preferred embodiment, the invention relates to a flavor-improving composition comprising a polypepfide with carboxypeptidase activity. In another preferred embodiment, the flavor-improving composition further comprises an endopeptidase. In another preferred embodiment, the flavoring composition further comprises one or more unspecific-acting endo- and/or exo-peptidase enzymes. In another preferred embodiment, the flavoring composition further comprises one or more specific-acting endo- and/or exo-peptidase enzymes.

In a preferred embodiment, the specific acting proteolytic enzyme is an endopeptidase such as a glutamyl endopeptidase (EC 3.4.21.19); a lysyl endopeptidase (EC 3.4.21.50); a leucyl endopeptidase (EC 3.4.21.57); a glycyl endopeptidase (EC 3.4.22.25); a prolyl endopeptidase (EC 3.4.21.26); trypsin (EC 3.4.21.4) or a trypsin-like (lysine/arginine specific) endopeptidase; or a peptidyl-Asp metalloendopeptidase (EC 3.4.24.33).

The glutamyl endopeptidase (EC 3.4.21.19) may preferably be obtained from a strain of Bacillus, in particular *Bacillus licheniformis* and *Bacillus subtilis*, a strain of Staphylococcus, in particular *Staphylococcus aureus*, a strain of Streptomyces, in particular *Streptonyces thermovulgaris* and *Streptomyces griseus*, or a strain of Actinomyces sp.

The lysyl endopeptidase (EC 3.4.21.50) may preferably be obtained from a strain of Achromobacter, in particular *Achromobacter tyticus*, a strain of Lysobacter, in particular *Lysobacter enzymogenes*, or a strain of Pseudomonas, in particular *Pseudomonas aeruginosa*.

The leucyl endopeptidase (EC 3.4.21.57) may be of plant origin.

The glycyl endopeptidase (EC 3.4.22.25) may preferably be obtained from the papaya plant (*Carica papaya*).

The prolyl endopeptidase (EC 3.4.21.26) may preferably be obtained from a strain of Flavobacterium, or it may be of plant origin.

The trypsin-like endopeptidase may preferably be obtained from a strain of Fusarium, in particular *Fusarium oxysporum*, e.g., as described in WO 89/06270 or WO 94/25583.

The peptidyl-Asp metalloendopeptidase (EC 3.4.24.33) may preferably be obtained from a strain of Pseudomonas, in particular *Pseudomonas fragi*.

In another preferred embodiment, the specific acting proteolytic enzyme is an exopeptidase that may act from either end of the peptide.

In a preferred embodiment, the specific acting proteolytic enzyme is an aminopeptidase such as a leucyl aminopeptidase (EC 3.4.11.1); or a tripeptide aminopeptidase (EC 3.4.11.4).

In another preferred embodiment, the specific acting proteolytic enzyme is a carboxypeptidase such as a proline carboxypeptidase (EC 3.4.16.2); a carboxypeptidase A (EC 3.4.17.1); a carboxypeptidase B (EC 3.4.17.2); a carboxypeptidase C (EC 3.4.16.5); a carboxypeptidase D (EC 3.4.16.6); a lysine (arginine) carboxypeptidase (EC 3.4.17.3); a glycine carboxypeptidase (EC 3.4.17.4); an alanine carboxypeptidase (EC 3.4.17.6); a glutamate carboxypeptidase (EC 3.4.17.11); a peptidyl-dipeptidase A (EC 3.4.15.1); or a peptidyldipeptidase (EC 3.4.15.5).

The polypeptide compositions may be prepared in accordance with methods known in the art and may be in the form of a liquid or a dry composition. The polypeptide may be stabilized by methods known in the art.

The present invention also relates to food products, e.g., baked products, comprising a protein hydrolysate obtained by the methods of the present invention. Such food products exhibit enhanced organoleptic qualities, such as improvement in flavor, palatability, mouth feel, aroma and crust color.

In the present context, the term "baked products" includes any food prepared from dough, either of a soft or a crisp character. Examples of baked products, whether of a white, light or dark type, which may be advantageously produced by the present invention, are bread, in particular white, whole-meal or rye bread, typically in the form of loaves or rolls; French baguette-type breads; pita breads; tacos; cakes; pancakes; biscuits; crisp breads; and the like.

Such baked products are conventionally prepared from a dough which comprises flour and water, and which is typically leavened. The dough may be leavened in various ways, such as by adding sodium bicarbonate or the like, or by adding a leaven (fermenting dough), but the dough is preferably leavened by adding a suitable yeast culture such as a culture of Saccharomyces cerevisiae (baker's yeast). Any of the commercially available Saccharomyces cerevisiae strains may be employed.

Further, the dough used in the preparation of the baked products may be fresh or frozen. The preparation of frozen dough is described by K. Kulp and K. Lorenz in "Frozen and Refrigerated Doughs and Batters". A flavor improving composition of the present invention is typically included in the dough in an amount in the range of 0.01–5%, more preferably 0.1–3%.

In the methods of the present invention, a polypeptide of the present invention, an endopeptidase, a transglutaminase, a peptidoglutaine, one or more specific and/or unspecific acting endo- and/or exo-peptidase enzymes, and/or one or more enzymes specified above may be added, either separately or concurrently, to the mixture from which the dough is made or to any ingredient, e.g., flour, from which the dough is to be made.

The present invention fuirther relates to a pre-mix, e.g., in the form of a flour composition, for dough and/or baked products made from dough, wherein the pre-mix comprises a flavor-improving composition of the invention and optionally one or more other enzymes specified above.

In another embodiment, the pre-mix comprises a hydrolysate obtained by the methods of the invention.

The pre-mix may be prepared by mixing the relevant enzymes with a suitable carrier such as flour, starch, a sugar or a salt. The pre-mix may contain other dough-improving and/or bread-improving additives.

In the present context, the term "pre-mix" is a mixture of baking agents, normally including flour, which has been prepared to permit storage under designated conditions and provide convenience in handling during dough preparation processes. Such a pre-mix may be of advantageous use in industrial and commercial bread-baking plants and facilities, as well as in retail bakeries.

The present invention also relates to the use of a hydrolysate produced by the methods of the invention as an additive to food products, such as baked foods, to enhance organoleptic qualities, such as flavor, palatability and aroma.

The hydrolysates enriched in free glutamic acid and/or peptide bound glutamic acid residues obtained by the methods of the present invention may be used in various industrial applications, in particular, where there is a need for the incorporation of functional proteins.

For example, the present invention also relates to food products comprising a hydrolysate enriched in free glutamic acid and/or peptide bound glutamic acid residues obtained by the method of the invention and to animal feed additives comprising a hydrolysate enriched in free glutamic acid and/or peptide bound glutamic acid residues obtained by the methods of the present invention.

The present invention is further described by the following examples which should not be construed as limiting the scope of the invention.

EXAMPLES

Materials

Chemicals used as buffers and substrates are commercial products of at least reagent grade.

Example 1

Purification of FLAVOURZYME™ Carboxypeptidase I

Carboxypeptidase was purified from a FLAVOURZYME™ broth (Novo Nordisk A/S, Bagsverd, Denmark). First, the broth (20 ml; 720 mg protein) was diluted with 180 ml of 20 mM sodium phosphate pH 7.0 buffer and filtered using Nalgene Filterware equipped with a 0.45 mm filter. The filtered solution was loaded onto a 24×130 mm column containing 31 ml of Q-Sepharose, Big Beads ("Phannacia Biotech AB", Uppsala, Sweden) pre-equilibrated with 20 mM sodium phosphate pH 7.0 buffer. The carboxypeptidase was eluted using a pH gradient from 7.0 (20 mM sodium phosphate buffer) to 5.0 (20 mM sodium acetate buffer) and then from 5.0 to 3.6 (20 mM sodium acetate buffer). Carboxypeptidase activity was monitored at 340 nm using 1.5 mM furylacryloyl-Ala-Lys as substrate at 50 mM sodium phosphate pH 6.0 buffer. Fractions between pH 4.3 and 3.6 were collected, pooled, and concentrated to 25 ml using ultrafiltration (Diaflo membranes, 10PK).

The concentrated solution was diluted with 100 ml of 20 mM sodium phosphate pH 7.0 buffer and then loaded onto a 20×100 mm column containing MonoQ Beads ("Pharmacia Biotech AB", Uppsala, Sweden) pre-equilibrated with 20 mM sodium phosphate pH 7.0 buffer. The carboxypeptidase was eluted with a 0 to 1 M NaCl gradient in 20 mM sodium phosphate pH 7.0 buffer. Fractions were monitored for carboxypeptidase activity as described above. The fractions between 0.10 and 0.13 M NaCl were collected, pooled, and concentrated using ultrafiltration against 20 mM sodium acetate pH 4.0 buffer.

The purified preparation was estimated to be at least 95% homogeneous based on SDS PAGE analysis. The major band was found to have a molecular weight of approximately 68 kDa (range of 66–70 kDa).

Example 2
Protein Sequencing and Amino Acid Analysis Methods

N-terminal sequencing of the purified carboxypeptidase and a degraded fragment of the carboxypeptidase from the broth of Example 1 was performed on an Applied Biosystems 476A Protein Sequencer (Perkin Elmer/Applied Biosystems Division, Foster City, Calif.) within on-line HPLC and liquid phase trifluoroacetic acid (TFA) delivery. Samples of the purified carboxypeptidase were transblotted onto Novex PVDF membranes (Novex, San Diego, Calif.) from SDS-PAGE gels and sequenced from a blott cartridge using sequencing reagents (Perkin Elmer/Applied Biosystems Division, Foster City, Calif.). Detection of phenylthiohydantoin-amino acids was accomplished by on-line HPLC using Buffer A containing 3.5% tetrahydrofuran in water with 15–30 mls of the Premix concentrate (Perkin Elmer/Applied Biosystems Division, Foster City, Calif.) containing acetic acid, sodium acetate, and sodium hexanesulfonate and Buffer B containing acetonitrile. Data was collected and analyzed on a Macintosh IIsi using Applied Biosystems 610 Data Analysis software.

The purified carboxypeptidase was also subjected to cyanogen bromide to generate peptide fragments of the enzyme for sequencing. The carboxypeptidase was digested with cyanogen bromide by reconstituting a dried sample of the purified carboxypeptidase in 70% formic acid with a few crystals of cyanogen bromide and incubating for 18 hours at room temperature in the dark. The peptide fragments were separated by SDS-PAGE electrophoresis using 10–20% Novex Tricine gels (Novex, San Diego, Calif.) and sequenced as described above.

N-terminal sequencing of the carboxypeptidase reveals that the N-terminus was blocked. The degraded fragment has the following amino acid sequence where amino acid residues in parentheses are not 100% certain and residues marked with a ? could not be determined. Amino acid residues underlined match 100% with the carboxypeptidase S1 from *Penicillium janthienellum*:

Peptide 1: ?<u>YGGHYGPAE</u>(F)NH(F)(Y)(E)(Q)(<u>N</u>)E(R) (SEQ ID NO:3)

Sequencing of the cyanogen bromide fragments showed the following peptide fragment sequences which are 30–40% homologous to the carboxypeptidase from *Penicillium janthinellum* (Svendsen et al., 1993, *FEBS Letters* 333: 39–43):

Peptide 2 (50 kDa): DAIGVNI?YTQ?NNDVYYA (SEQ ID NO:4)
Peptide 3 (42 kDa): DAIGVNI(N)YTQSNN(D) VYYAFQQTGDFVWPNFIEDL (SEQ ID NO:5)
Peptide 4 (17 kDa): (?C)RDNVEGP(?) YAFAGRGVYDIRHPYD(P)(D)(T) (SEQ ID NO:6)

Example 3
Characterization of Purified Carboxypeptidase I

Inhibition of the carboxypeptidase with 1,10-phenanthroline and phenylmethylsulfonyl fluoride was evaluated using firylacryloyl-Ala-Lys as substrate at pH 7.0 in 20 mM phosphate buffer where hydrolysis was monitored at 340 nm.

The results indicate that 1,10-phenanthroline does not inhibit the carboxypeptidase activity. On the other hand, phenylmethylsulfonyl fluoride inhibits carboxypeptidase activity completely at pH 7.0 using furylacryloyl-Ala-Lys as a substrate. These results suggest that carboxypeptidase was a serine protease.

Using N-CBZ-Ala-Ile as substrate in 50 mM sodium acetate buffer (pHs 4–7.5) and 50 mM citric acid/KH$_2$PO$_4$ buffer (pHs 2.9 and 3.9), the pH dependence of the bimolecular constant k$_{cat}$/K$_m$ at 25° C. was a bell-shaped curve with a pronounced optimum at pH 4.0–4.5 (FIG. 1). The slope of the right and the left branches of the curve appears to be -1 and 1, respectively, which indirectly shows that the active center of the enzyme contains two ionogenic groups with pK values of 3.3 and 5.7.

Figure 2:
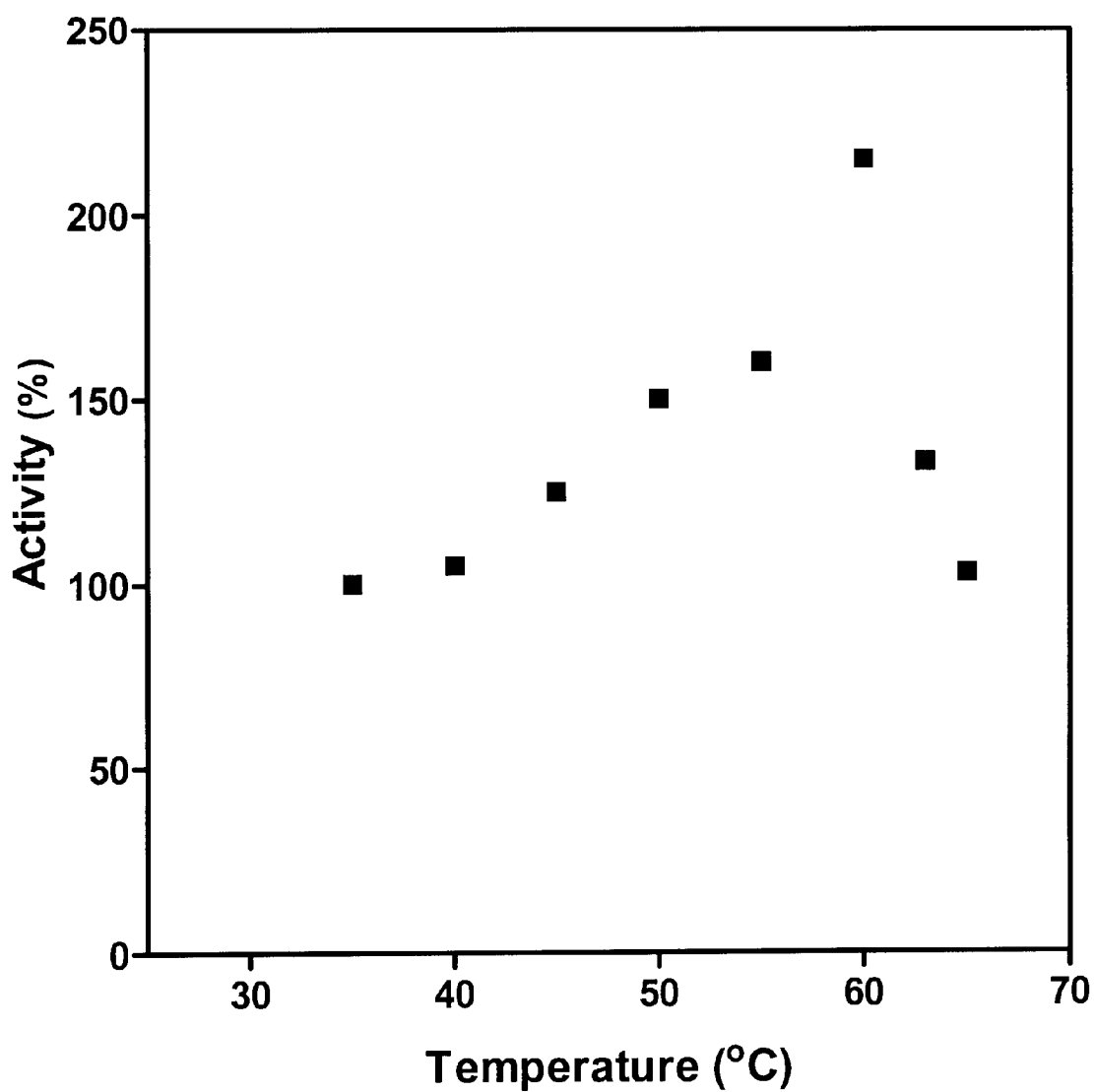
FIG. 2 shows the dependence of *Aspergillus oryzae* ATCC 20386 carboxypeptidase I activity on temperature.

The dependence of temperature on the activity of the *Aspergillus oiyzae* ATCC 20386 carboxypeptidase I was determined using N-CBZ-Ala-Ile as substrate in 50 mM sodium acetate pH 4 buffer. The results as shown in FIG. 2 indicate optimal activity is observed at a temperature in the range of about 55° C. to about 60° C. at pH 4.

The substrate specificity of the carboxypeptidase was determined by measuring the hydrolysis of a substrate listed in Table 1 at pH 4.0 in 50 mM acetate buffer. o-Phthaldialdehyde together with dithiothreitol were used to monitor the liberation of free Ile, Glu, Lys, Arg, Asp, Asn, Gly, Phe, amd Tyr under enzymatic hydrolysis according to the procedure of Roth, M., 1971, *Analytical Chemistry* 43: 880. The k$_{cat}$ value for the hydrolysis of N-CBZ-Ala-X or N-CBZ-Glu-X was determined based on the assumption that molecular weight of the carboxypeptidase was 68 kD and that the enzyme preparation was homogeneous.

The carboxypeptidase was determined to have very broad substrate specificity where no preference for aromatic, bulky aliphatic, or polar carboxyl-terminal amino acid residues was observed. The best substrates of the carboxypeptidase, N-CBZ-Ala-Glu, N-CBZ-Ala-Ile, N-CBZ-Ala-Lys, N-CBZ-Ala-Arg, and N-CBZ-Ala-Asn, have very different terminal amino acid residues but similar values of all kinetic parameters for the specific hydrolysis at pH 4.0 (Table 1).

TABLE 1

Substrate specificity of the carboxypeptidase.

| Substrate | K$_m$ 10$^3$ (M) | k$_{cat}$$^b$ (s$^{-1}$) | k$_{cat}$/K$_m$ 10$^3$ (M$^{-1}$ s$^{-1}$) |
|---|---|---|---|
| N-CBZ-Ala-Ile | 0.11 | 24 | 218 |
| N-CBZ-Ala-Glu | 0.10 | 32 | 320 |
| N-CBZ-Ala-Lys | 0.12 | 32 | 270 |
| N-CBZ-Ala-Arg | 0.11 | 27 | 246 |
| N-CBZ-Ala-Asp | 0.27 | 27 | 100 |
| N-CBZ-Ala-Asn | 0.09 | 19 | 216 |
| N-CBZ-Ala-Gly | 0.92 | 5.5 | 6 |
| N-CBZ-Ala-Phe | 0.24 | 17 | 72 |
| N-CBZ-Ala-Tyr | 0.09 | 17.5 | 194 |
| N-CBZ-Glu-Tyr | 0.11 | 4.7 | 43 |

The carboxypeptidase also was able to cleave Pro from N-CBZ-Ala-Pro. However, the specificity of the enzyme to this substrate was low. Only 16% of a 2 mM N-CBZ-Ala-Pro solution was hydrolyzed after a 2 hour incubation with a very high concentration (4.9×10$^{-7}$ M) of the carboxypeptidase. N-CBZ-Ala-Phe was a good substrate for the carboxypeptidase. The value of k$^{cat}$ was at least 8.5-fold higher than that for the acid carboxypeptidases O-1 and O-2 from *Aspergillus oryzae*. (Takeuchi and Ichishima, 1981, *Agric. Biol. Chem.* 45: 1033, Takeuchi et al., 1982, *Current Microbiology* 7: 19).

The K$_m$ value of the carboxypeptidase toward furylacryloyl-Ala-Lys was 0.4 mM at pH 4.0, 25° C.

The carboxypeptidase also possesses high thermostability. A 10 minute incubation of the enzyme in 50 mM acetate buffer at pH 4.0 and 60° C. results in a 65% residual activity compared to the 37 kDa carboxypeptidase from *Aspergillus oryzae* which was completely inactivated at this temperature (Azarenkova et al., 1976, *Biokhimia* 41: 20). A 10 minute incubation of the enzyme in 50 mM acetate buffer at pH 4.0 and 55° C. results in a 74% residual activity.

The activity of the carboxypeptidase was determined by measuring the rate of specific hydrolysis of N-CBZ-Ala-Glu. One carboxypeptidase unit (CPDU) is the amount of carboxypeptidase which liberates 1 micromole of glutamate per minute from a 0.5 mM N-CBZ-Ala-Glu solution at pH 4.5 and 25° C. A reagent containing o-phthaldialdehyde in combination with dithiothreitol was used to monitor the liberation of free glutamate under enzymatic hydrolysis according to the procedure of Roth, 1971, supra. The o-phthaldialdehyde reagent was a solution of o-phthaldialdehyde (6 mM) and dithiothreitol (6.5 mM) in 0.1 M sodium tetraborate. Briefly, 0.05 ml of the enzyme solution in 20 mM acetate buffer, pH 4.5 was incubated with 1 ml of substrate. At regular time intervals, a 0.3 ml aliquot was withdrawn, mixed with 0.9 ml of the o-phthaldialdehyde reagent, and the absorption at $A_{340}$, using a path length of 1 cm, of the resultant product was measured. Where the dependence of $A_{340}$ on the incubation time was linear, the specific activity of the enzyme was calculated using the equation: specific activity=slope (optical density per min)×11.35. By this procedure, the specific activity of the purified carboxypeptidase was determined to be 11 CPDU per mg protein which is equivalent to 11 micromoles glutamate per minute per mg protein.

Example 4

RNA Isolation

Aspergillus oryzae strain ATCC 20386 was cultivated in a fermentation tank in a medium comprised of 7.5 g of potato starch, 10 g of soy bean meal, 2 g of $KH_2PO_4$, 5 g of $Na_2HPO_4$-2 $H_2O$, and 0.1 g of $ZnSO_4$-7 $H_2O$ per liter. A two liter sample was taken after five days of growth at 30° C., and the mycelia were collected, frozen in liquid $N_2$, and stored at −80° C. Total RNA was prepared from the frozen, powdered mycelium of Aspergillus oryzae ATCC 20386 by extraction with guanidinium thiocyanate followed by ultracentrifugation through a 5.7 M cesium chloride cushion (Chirgwin et al., 1979, Biochemistry 18: 5294–30 5299). Poly(A)+ RNA was isolated by oligo(dT)-cellulose affinity chromatography according to Aviv and Leder (1972, Proceedings of the National Academy of Sciences USA 69: 1408–1412).

Example 5

Construction of a cDNA Library

Double-stranded cDNA was synthesized from 5 µg of Aspergillus oryzae ATCC 20386 poly(A)+ RNA of Example 4 as described by Gubler and Hoffinan (1983, Gene 25: 263–269) and Sambrook et al. (1989, Molecular Cloning: A Laboratory Manual, Cold Spring Harbor Press, Cold Spring Harbor, N.Y.), except that an oligo(dT)-NotI anchor primer, instead of an oligo(dT)12–18 primer, was used in the first strand reaction. After synthesis, the cDNA was treated with Mung bean nuclease (Life Technologies, Gaithersburg, Md.), blunt-ended with T4 DNA polymerase (Boehringer Mannheim, Indianapolis, Ind.), and ligated to non-palindromic BstXI adaptors (Invitrogen, San Diego, Calif.), using about 50-fold molar excess of the adaptors. The adapted cDNA was digested with NotI, size-fractionated for 1.2–3.0 kb cDNAs by agarose gel electrophoresis, and ligated into BstXI/NotI cleaved pYES2.0 vector (Invitrogen, San Diego, Calif.). The ligation mixture was used to transform electrocompetent E. coli DH10B cells (Life Technologies, Gaithersburg, Md.) according to the manufacturer's instructions. The library consisting of 1×10⁶ independent clones was stored as individual pools (25,000–30,000 colony forming units/pool) in 20% glycerol at −80° C., and as double stranded cDNA and ligation mixture at −20° C.

Example 6

PCR Amplification of Aspergillus oryzae ATCC 20386 Carboxypeptidase I

Based on the amino acid sequences of the Aspergillus oryzae ATCC 20386 carboxypeptidase I partial peptides described in Example 2, the degenerate oligonucleotide primers shown below were synthesized with an Applied Biosystems Model 394 DNA/RNA Synthesizer, according to the manufacturer's instructions, for use to PCR amplify carboxypeptidase I gene fragments from Aspergillus oryzae ATCC 20386:

Forward primer: 5'-TAYGGNGGICAYTAYGGICCNG-3' (SEQ ID NO:7)

Reverse primer: 5'-ATRAARTHIGGCCAIACRAARTC-3' (SEQ ID NO:8)

(R=A or G, Y=C or T, N=G or A or C or T, I=Inosine)

Amplification reactions (100 µl) were prepared using approximately 1 µg of isolated plasmids from an Aspergillus oryzae ATCC 20386 cDNA library of Example 5 as the template. Each reaction contains the following components: 1 µg plasmids, 40 pmol forward primer, 40 pmol reverse primer, 200 µM each of dATP, dCTP, dGTP, and dTTP, 1×Taq polymerase buffer (Perkin-Elner Corp., Branchburg, N.J.), and 2.5 Units of Taq polymerase (Perkin-Elmer Corp., Branchburg, N.J.). The reactions were incubated in a Perkin-Elmer Model 480 Thermal Cycler programmed as follows: Cycle 1—95° C. for 5 minutes, 45° C. for 2 minutes, and 67° C. for 2 minutes; and Cycles 2–30—95° C. for 2 minutes; 45° C. for one minute, and 67° C. for 2 minutes. The reaction products were isolated on a 1% agarose gel (Eastman Kodak, Rochester, N.Y.). The 550 bp product band was excised from the gel and purified using GenElute spin columns (Supelco, Bellefonte, Pa.) according to the manufacturer's instructions. The purified PCR products were subsequently cloned into a pCRII vector (Invitrogen, San Diego, Calif.) and the DNA sequences were determined using lac forward and reverse primers (New England BioLabs, Beverly, Mass.).

A carboxypeptidase I gene segment consisting of approximately 186 codons (550 bp) was amplified from Aspergillus oryzae ATCC 20386 as shown in FIG. 1 with the carboxypeptidase-specific PCR primers described above. DNA sequence analysis shows that the amplified gene segment encodes a portion of the corresponding Aspergillus oryzae ATCC 20386 carboxypeptidase I gene. The carboxypeptidase I gene segment was used to probe an Aspergillus oryzae ATCC 20386 cDNA library.

Example 7

Identification of Carboxypeptidase I Clones

The Aspergillus oryzae ATCC 20386 cDNA library was plated on Luria agar plates supplemented with 50 mg/ml carbenicillin. Colony lifts (Maniatis et al., 1982, Molecular Cloning, A Laboratory Manual, Cold Spring Harbor Press, Cold Spring Harbor, N.Y.) were performed on approximately 5,000 colonies and the DNA was cross-linked onto membranes (Hybond N+, Amersham, Arlington Heights, Ill.) using a UV Stratalinker (Stratagene, La Jolla, Calif.). The membranes were soaked for three hours at 45° C. in a hybridization solution containing 5×SSPE, 0.3% SDS, 50% formamide, and 10 mg/ml of denatured and sheared herring sperm DNA. The carboxypeptidase I gene fragment isolated from the Aspergillus oryzae ATCC 20386 as described in Example 1 was radiolabeled using the Random Primed DNA Labeling Kit (Boehringer Mannheim, Mannheim, Germany), denatured by adding NaOH to a final concentration of 0. 1M, and added to the hybridization solution at an activity of approximately 1×10⁶cpm per ml of hybridization solution. The mixture was incubated overnight at 45° C. in a shaldng water bath. Following incubation, the membranes were washed once in 2×SSC with 0.2% SDS at 55° C. followed by two washes in 2×SSC at the same temperature. The membranes were dried on blotting paper for 15 minutes, wrapped in SaranWrap™, and exposed to X-ray film overnight at −70° C. with intensifying screens (Kodak, Rochester, N.Y.).

Six colonies, designated *E. coli* DH5a clones EJG12, EJG12A, EJG12B, EJG12C, EJG12D, and EJG12E, produced strong hybridization signals with the probe. The six colonies were inoculated into three ml of LN+50 μg/ml carbenicillin medium and grown overnight at 37° C. Miniprep DNA was prepared from each of these clones using the Wizard 373 DNA Purification Kit (Promega, Madison, Wis.). The carboxypeptidase encoding plasmids were confirmed by DNA sequencing.

Example 8

DNA Sequence Anaysbs of *Aspergillus oryzae* ATCC 20386 Carboxypeptidase I Gene

DNA sequencing of the carboxypeptidase I clone (*E. coli* DH5a EJG12) described in Example 2 was performed with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virology Methods* 38: 47–60). Oligonucleotide sequencing primers were designed to complementary sequences in the carboxypeptidase I gene and were synthesized on an Applied Biosystems Model 394 DNA/RNA Synthesizer according to the manufacturer's instructions.

The nucleotide sequence of the gene encoding the *Aspergillus oryzae* ATCC 20386 carboxypeptidase I cDNA is shown in FIG. 3 (SEQ ID NO:1). Sequence analysis of the cloned insert revealed a large open reading frame of 1665 nucleotides (excluding the stop codon) encoding a protein of 555 amino acids. The G+C content of this open reading frame was 52.1%. Based on the rules of van Heijne (van Heijne, 1984, *Journal of Molecular Biology* 173: 243–251), the first 18 amino acids likely comprise a secretory signal peptide which directs the nascent polypeptide into the endoplasmic reticulum (double underlined in FIG. 3).

The deduced amino acid sequence of the *Aspergillus oryzae* ATCC 20386 carboxypeptidase I as shown in FIG. 3 (SEQ ID NO:2) indicates that the calculated molecular weight of the primary translation product is 61.2 kDa which is consistent with the estimate of 68 kDa based on the mobility of the purified protein on SDS-PAGE. Amino acid sequences of peptides obtained from the purified carboxypeptidase I as described in Example 2 are underlined in FIG. 3 and consistent with those found in the deduced amino acid sequence of the *Aspergillus oryzae* ATCC 20386 carboxypeptidase I cDNA.

Using the Clustal alignment program (Higgins, 1989, CABIOS5: 151–153) to compare the deduced amino acid sequence of the *Aspergillus oryzae* ATCC 20386 carboxypeptidase I to that of other fungal carboxypeptidases reported in the literature, a 38.8% identity is observed compared to the *Penicillium janthinellum* carboxypeptidase S1 (Svendsen et al., 1993, supra) (SEQ ID NO:9), 13.3% identity to the *Penicillium janthinellum* carboxypeptidase S3 (Svendsen and Day, 1995, *FEBS Letters* 371: 1–3) (SEQ ID NO:10), 16.4% identity to the *Aspergillus phoenicis* carboxypeptidase (Chiba et al., 1995, *Biochemical Journal* 308: 405–409) (SEQ ID NO:11), and 14.7% identity to the *Aspergillus niger* carboxypeptidase (van den Hombergh et al., 1994, *Gene* 151: 73–79) (SEQ ID NO:12), as shown in FIG. 4. The deduced amino acid sequence for *Aspergillus oryzae* carboxypeptidase I has a catalytic triad comprising Asp-His-Ser (starred in FIG. 4), which is conserved among serine carboxypeptidases.

Example 9

Cross-hybridization Studies Using Genomic DNA from Other Fungi

The cloned *Aspergillus oryzae* ATCC 20386 carboxypeptidase gene was used as a probe in Southern hybridization experiments with genomic DNA samples from a variety of fungal genera. Southern blots were probed under conditions of low stringency (25% formamide, 5×SSPE, 0.3% SDS at 45° C.), medium stringency (35% formamide, 5×SSPE, 0.3% SDS at 45° C.) and high stringency (50% formamide, 5×SSPE, 0.3% SDS at 45° C.). Genomic DNA samples were isolated from the following species using the protocol outlined below: *Aspergillus niger* (Bo-95), *Aspergillus oryzae* (A1560), *Penicillium purpurogenum* (A3191), *Penicillium rubrum* (CBS 433.62), *Humicola grisea* var. thermoidea (ATCC 16453), *Botrytis cinerea* (ATCC 11542), *Curvularia verruculosa* (CBS 147.63), *Rhizoctonia solani* (IMI 358730), *Trichoderma harzianum* (CBS 819.68), *Absidia griseola* (ATCC 22618), *Myrothecium verrucaria* (ATCC 9095), *Myceliophthora thermophila* (CBS 117.65), and *Penicillium varians* (CBS 386.48).

Each of the strains described above was grown in 25 ml of 0.5% yeast extract-2% glucose (YEG) medium for 24 hours at 32° C. and 250 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powders were added to 20 ml of TE buffer and 5 ml of 20% w/v sodium dodecylsulfate (SDS) in a disposable plastic centrifuge tube. The mixtures were gently inverted several times to insure mixing, and extracted twice with an equal volume of phenol:chloroform:isoamyl alcohol (25:24:1 v/v/v). Sodium acetate (3 M solution) was added to a final concentration of 0.3 M followed by addition of 2.5 volumes of ice cold ethanol to precipitate the nucleic acids. The nucleic acids were then pelleted by centrifuging the tube at 15,000×g for 30 minutes. The pellets were allowed to air dry for 30 minutes before resuspension in 0.5 ml of TE buffer. DNase-free ribonuclease A was added to a concentration of 100 mg/ml and the mixtures were incubated at 37° C. for 30 minutes. Proteinase K was then added at a concentration of 200 mg/ml and the mixtures were incubated an additional hour at 37° C. Finally, the mixtures were extracted twice with phenol:chloroform:isoamyl alcohol (25:24:1 v/v/v) before precipitating the DNA with sodium acetate and ethanol as described earlier. The DNA pellets were dried under vacuum, resuspended in TE buffer, and stored at 4° C. until further use.

Each DNA sample (ca. 5 micrograms) was digested with BamHI and EcoRI prior to electrophoresis on a 1% agarose gel. The DNA was blotted to Zeta-Probe nylon membrane (BioRad Laboratories, Hercules, Calif.) and probed with a nick translated DNA probe comprising the carboxypeptidase I gene. The blots were washed for 30 minutes in 2×SSC+ 0.2% SDS at 45° C., and for 30 minutes in 2×SSC (no SDS). The washed filter was exposed to X-ray film overnight at −70° C. with intensifing screens.

The carboxypeptidase gene from *Aspergillus oryzae* ATCC 20286 cross-hybridized with probable carboxypeptidase gene sequences in several other fungal species (Table 2). Under conditions of low stringency strong hybridization signals were apparent in DNAs from *Aspergillus oryzae* A1560, *Aspergillus niger*, and Botrytis cinerea. Weaker signals were detected in *Curvularia verruculosa, Humicola grisea* var. thermoidea, *Myrothecium verrucaria*, and *Trichoderma harzianum*. No hybridization was detected in *Absidia griseola, Myceliophthora thermophila, Penicillium purpurogenum, Penicillium rubrum, Penicillium varians*, or *Rhizoctonia solani*. Using medium stringency, strong hybridization signals were visible with only *Aspergillus oryzae* A1560 and *Botrytis cinerea*. Weak hybridization was observed with DNAs from *Aspergillus niger, Curvularia verruculosa, Humicola grisea* var. thermoidea, and *Myrothecium verrucaria*. Under high stringency conditions, only DNA from *Aspergillus oryzae* A1560 hybridized with the carboxypeptidase gene probe. These data indicated that the *Aspergillus oryzae* ATCC 20286 carboxypeptidase gene can be used as a probe to clone carboxypeptidase genes from other filamentous fungi.

TABLE 2

Hybridization of genomic DNA samples from various fungi probed with the cloned *Aspergillus oryzae* ATCC 20286 carboxypeptidase gene.
A +++ denotes a strong positive hybridization signal,
+ denotes a weak signal, and – denotes no detectable hybridization.

| Genomic DNA Source | Low Stringency | Medium Stringency | High Stringency |
|---|---|---|---|
| *Absidia griseola* | – | – | – |
| *Aspergillus niger* | +++ | + | – |
| *Aspergillus oryzae* A1560 | +++ | +++ | +++ |
| *Botrytis cinerea* | +++ | +++ | – |
| *Curvularia verruculosa* | + | + | – |
| *Humicola grisea* var. *thermoidea* | + | + | – |
| *Myceliophthora thermophila* | – | – | – |
| *Myrothecium verrucaria* | + | + | – |
| *Penicillium purpurogenum* | – | – | – |
| *Penicillium rubrum* | – | – | – |
| *Penicillium varians* | – | – | – |
| *Rhizoctonia solani* | – | – | – |
| *Trichoderma harzianum* | + | – | – |

Example 10
Protein Hydrolysis by a Polypeptide Having Carboxypeptidase Activity

Commercial grade soy meal, wheat gluten, casein and gelatin were used as protein substrates. The soy meal was prepared from defatted toasted soy grits 20/80/20 (Cargill BV, NL); vital wheat gluten was obtained from Crespel and Dieters, Denmark; casein was obtained as Na-Caseinate Miprodan (MD Foods, Denmark); and gelatin was obtained as Bonegelatin (DGF Stores, Denmark).

The substrates were prepared as a 2% (w/v) aqueous solution, in which the protein concentration was determined by the method of Kjeldahl. Two hundred mg of each substrate, obtained in the form of a dry composition, was dissolved in 9 ml of tap water and the pH was adjusted to 7.0. One ml of an enzyme solution was added containing either FLAVOURZYME™ (3 LAPU), carboxypeptidase (11.5 CPDU), or the combination of the two. The reaction mixture was incubated for 18 hours at 50° C. The mixtures were then inactivated by heating to 85° C. for 3 minutes.

The hydrolysates were cooled and the degree of hydrolysis (DH) was assayed in microtiter plates using OPA (ortho-phtaldialdehyde, Sigma Chemical Co., St. Louis, Mo.) as the detecting reagent. The DH, defined as described in by Adler-Nissen (1986, *Enzymic hydrolysis of Food Proteins*, Elsevier Applied Science Publishers), was determined by reaction of the supernatant with OPA (ortho-phtaldialdehyde, Sigma Chemical Co., St. Louis, Mo.). For the OPA reagent, 160 mg of OPA was dissolved in 4 ml of ethanol and transferred to a 200 ml volumetric flask containing a solution of 7.62 g of disodium tetraborate decahydrate, 200 mg of sodium dodecylsulphate, and 176 mg of dithiothreitol and the flask was filled to 200 ml with water.

A volume of 25 µl of suitably diluted supernatant was mixed with 200 µl of OPA reagent in a microtiter plate well and allowed to react for exactly 2 minutes at 25° C. The absorbance at 340 nm was measured in a microtiter plate reader and compared to the absorbance of a 95 mM L-serine standard solution after subtraction of the blank value (water reacted with OPA-reagent). To determine the true DH, the serine equivalents measured in the supernatants were corrected with the factors suggested by Adler-Nissen for the trinitrobenzenesulfonic acid method (Adler-Nissen, 1979, *Agricultural and Food Chemistry* 17: 1256) which gave the same response as the described OPA method. The degree of hydrolysis was calculated on basis of the total amount of protein in the hydrolysis mixture (not on basis of soluble protein).

The results, summarized in Table 3 below, indicate that for all substrates carboxypeptidase alone has no effect, but when added with FLAVOURZYME™ enhanced the DH obtained by FLAVOURZYME™.

TABLE 3

| Substrate Enzyme | Casein DH | Gelatin DH | Soy Meal DH | Wheat Gluten DH |
|---|---|---|---|---|
| FLAVOURZYME | 44.8 | 20.2 | 36 | 41 |
| Carboxypeptidase | 0 | 0 | 0 | 0 |
| Flavourzyme + Carboxypeptidase | 50.2 | 22.9 | 40 | 45.6 |

Example 11
Increased Protein Solubility and Release of Glutamate by Deamidation

Wheat gluten (WG) was obtained from Cargill (JOB 5141) and deamidated wheat gluten (DWG) was obtained from StaPro Consultancy B.V., Lemdijk 32, 9422 TH Smilde, NL. Suspensions of 8% protein were made by mixing 11 g of gluten with 89 g of water. The pH was adjusted to 6.5 with NaOH. Glutamate/aspartate specific protease (SP446), obtainable as described in WO 91/13554, or lysine/arginine specific protease (SP387) obtainable as described in WO 89/06270, was added to the suspensions. The dosage was 0.01 AU/g protein for SP446 and 0.006 AU/g protein for SP387. FLAVOURZYME™ was added to some of the hydrolysates at a dosage of 20 LAPU/g protein. One LAPU (Leucine Amino Peptidase Unit) is the amount of enzyme which decomposes 1 micromole of L-leucine-p-nitroanilide per minute under the following conditions: 26 mM L-leucine-p-nitroanilide in 0.1 M Tris pH 8.0 buffer at 40° C. for 10 minutes. Upon hydrolysis, p-nitroanilide is liberated turning the solution yellow which is monitored 405 nm.

The hydrolyses were carried out at 50° C. without further pH adjustment for 18 hours. The enzymes were inactivated by heating at 85° C. for 15 minutes. The pH was adjusted to 5 and the hydrolysates were centrifuged. The content of protein and free glutamate in the supernatant was determined.

The protein content was determined by Kjeldahl analysis, using a Kjeldahl factor of 6.25.

The content of free glutamate was determined by use of a glutamate determination kit according to the manufacturer's instructions (Boehringer-Mannheim, Indianapolis, Ind.). The method was adapted for use in microfiter plates.

When comparing wheat gluten (WG) to deamidated wheat gluten (DWG), the results as shown in Table 4 demonstrated that deamidation increased the susceptibility of the gluten to specific proteases, such that more protein became soluble. By addition of FLAVOURZYME™ with a specific protease, the release of glutamate was doubled due to deamidation.

TABLE 4

| Hydrolysate | Protein Solubility % | | Glutamate Content (mg/l) | |
|---|---|---|---|---|
| | WG | DWG | WG | DWG |
| SP446 | 18 | 54 | 0 | 0 |
| SP387 | 35 | 44 | 0 | 0 |
| SP446 + FLAVOURZYME ™ | 34 | 87 | 1000 | 2000 |

Example 12
Enzymatic Deamidation and Release of Glutamate

Peptidoglutaminase II was produced by growing *Bacillus circulans* strain ATCC 21590 in shake flasks (400 ml) containing 200 ml of a medium composed of 1% polypeptone, 0.5% lactose, 0.025% $MgSO_4$-7 $H_2O$, 0.005% $FeSO_4$-7 $H_2O$, 0.025% $KH2PO_4$, and 17% $Na_2HPO_4$-12 $H_2O$ (pH adjusted to 7.2), at 30° C. for 20 hours with mixing at 270 rpm. The cells were harvested by centrifugation at 4000 rpm in 1 liter flasks. The cells were then frozen.

The purification of peptidoglutaminase II from *Bacillus circulans* was performed at room temperature. The frozen *Bacillus circulans* cells were thawed and suspended in Lysis buffer (50 mM Tris/HCl; 25% (w/v) sucrose; 1 mM EDTA, pH 8.0) until a homogeneous suspension was obtained —100 g wet cells per liter of Lysis buffer. Lysozyme (10 mg/ml) and DNAse I (Sigma DN-25, 10 mg/ml) were dissolved in Lysis buffer. Then 100 ml of lysozyme solution, 10 ml of 1.0 M $MgCl_2$, and 1 mnl of DNAse I solution were added per liter of cell suspension. The enzymes were allowed to act for 1 hour.

The suspension was filtered through a Seitz depth filter plate and the filtrate was transferred to a 10 mM $KH_2PO_4$/ NaOH, pH 8.0 (Buffer A) on a Sephadex G25 column (Pharrnacia). The enzyme solution was applied to a SOURCE Q column (Pharmacia) equilibrated in Buffer A and eluted with a linear NaCI gradient (0→500 mM) in Buffer A. Fractions from the column were analysed for Peptidoglutaminase II activity as described below and fractions with activity were pooled. The absorbance of the pooled fractions at 280 nm was 1.78, thus the protein content was estimated to 1.8 mg/ml.

The purity of the protein in the peptidoglutaminase II pool was approximately 25% as judged from a SDS-PAGE gel. Thus, the preparation contained approximately 0.5 mg/ml of pure peptidoglutaminase II.

The peptidoglutaminase activity was determined by measuring the ammonia formed during hydrolysis of γ-carboxyamide of N-tert-Butoxycarbonyl-Gln-Pro (N-t-BOC-Gln-Pro; SIGMA No. B-4403) using the Boehringer-Mannheim kit for ammonia determination (Cat. No. 1112732). In this kit, ammonia was measured by determination of the consumption of NADH by glutamate dehydrogenase, and blanks without the addition of N-t-BOC-Gln-Pro were also applied in order to subtract the effect of other NADH consuming enzymes.

A total of 200 mg of wheat gluten protein was added to 9 ml of boiling water and after cooling, the pH was adjusted to 7.0. Then 250 μl of the peptidoglutarminase II preparation (PEP) described above was added. The glutamate/aspartate specific protease (SP446) described in Example 11 was added in an amount of 0.04 AU/g protein, and FLA-VOURZYME™ described in Example 11 was added in an amount of 20 LAPU/g protein.

Hydrolysis was allowed to proceed without pH adjustment for 18 hours at 50° C. Controls without the addition of peptidoglutaminase were also run. The hydrolysates were centrifuged and glutamate was measured as described in Example 11.

The DH of the wheat gluten protein was determined as described in Example 10.

The results as shown below in Table 5 demonstrated that hydrolysis with the peptidoglutaminase preparation increased the DH as well as the release of glutamate.

TABLE 5

| Hydrolysis | DH % | Glutamate (mg/l) |
|---|---|---|
| Minus PEP | 40 | 131 |
| Plus PEP | 43 | 171 |

Example 13
Flavor Improvement of Soy Hydrolysates

The soy hydrolysates were prepared using an 8% soy meal protein concentration (1 or 0.2 liter) at 50° C. for 18 hours with no pH adjustment with ALCALASE™ 2.4L (Novo Nordisk, Bagsvxrd, Denmark) and a solution of purified carboxypeptidase (approximately 40 CPDU/ml) prepared as described in Example 1. The dosages were 1200 mg of ALCALASE™ per liter or 1200 mg of ALCA-LASE™ and 5 ml of carboxypeptidase per liter.

The enzymes were then inactivated at 93° C. for 15 minutes and analyzed for DH and glutamate as described in Examples 10 and 11, respectively. The pH was adjusted to 5 before maturation at 125° C. for 30 minutes. All hydrolysates were centrifuged after maturation.

The soy bean meal hydrolysates produced were evaluated by a trained taste panel. The supernatants were diluted 5.3 times and presented twice to eleven judges in randomised order. The judges evaluated on a scale from 0 to 9 the following flavor attributes: Bitterness, palatability, bouillon, meat, chicken, smoke, and MSG.

The DH results and the mean scores for the different flavor attributes are shown in Table 6.

TABLE 6

| Treatment | DH | bitterness | palatability | bouillon | meat | vegetable | chicken | smoke | MSG |
|---|---|---|---|---|---|---|---|---|---|
| Alcalase | 17.3 | 4.45 | 1.68 | 1.95 | 1.14 | 1.86 | 1.82 | 2.77 | 1.41 |
| Alcalase + CPD | 33.0 | 2.77 | 2.18 | 2.59 | 1.41 | 2.23 | 2.36 | 3.14 | 1.86 |

The bitternes results showed that addition of carboxypeptidase to ALCALASE™ significantly reduced bitterness. With respect to overall palatability, improvement was seen by adding carboxypeptidase to ALCALASET™.

Bouillon, chicken, and possibly MSG flavors were also improved by addition of carboxypeptidase to ALCALASE™. Meat, smoke, and vegetable flavors were also improved by the addition of carboxypeptidase.

Deposit of Biological Materials

The following biological material has been deposited under the terms of the Budapest Treaty with the Agricultural Research Service Patent Culture Collection, Northern Regional Research Center, 1815 University Street, Peoria, Ill., 61604, and given the following accession number:

| Deposit | Accession Number | Date of Deposit |
|---|---|---|
| E. coli DH5a pEJG12 | NRRL B-21616 | August 28, 1996 |

What is claimed is:

1. An isolated polypeptide having carboxypeptidase activity with (i) an optimal activity with respect to pH in the range of about pH 4.0 to about pH 5.0 at 25° C.; (ii) an optimal activity with respect to temperature in the range of about 55° C. to about 60° C. at pH 4; (iii) a residual activity of at least about 65.5% after 30 minutes at pH 4.0 and 60° C.; and (iv) an ability to hydrolyze X from N-CBZ-Ala-X wherein N-CBZ is N-carbobenzoxy and X is any amino acid, wherein the polypeptide is selected from the group consisting of:

(a) a polypeptide having an amino acid sequence which has at least 95% identity with amino acids 19 to 555 of SEQ ID NO:2;

(b) a polypeptide which is encoded by a nucleic acid sequence which hybridizes under medium stringency conditions with (i) nucleotides 55 to 1662 of SEQ ID NO:1, (ii) its complementary strand, or (iii) a subsequence thereof, wherein medium stringency conditions are defined as prehybridization and hybridization a 42° C. in 5×SSPE, 0.3% SDS, 200 mg/ml sheared and denatured salmon sperm DNA, and 35% formamide;

(c) an allelic variant of (a) or (b); and (d) a fragment of (a), (A), or (c), wherein the fragment has carboxypeptidase activity.

2. The polypeptide of claim 1, wherein X is selected from the group consisting of Ile, Glu, Lys, Arg, Asp, Asn, Phe, and Tyr.

3. The polypeptide of claim 1, having an amino acid sequence which has at least 95% identity with amino acids 19 to 555 of SEQ ID NO:2.

4. The polypeptide of claim 1, comprising the amino acid sequence of SEQ ID NO:2.

5. The polypeptide of claim 1, consisting of the amino acid sequence of SEQ ID NO:2 or a fragment thereof.

6. The polypeptide of claim 4, consisting of the amino acid sequence of SEQ ID NO:2.

7. The polypeptide of claim 1, which consists of amino acids 19 to 555 of SEQ ID NO:2.

8. The polypeptide of claim 1, which is encoded by a nucleic acid sequence which hybridizes under medium stringency conditions with (i) nucleotides 55 to 1662 of SEQ ID NO:1, (ii) its complementary strand, or (iii) a subsequence thereof, wherein medium stringency conditions are defined as prehybridization and hybridization a 42° C. in 5×SSPE, 0.3% SDS, 200 mg/ml sheared and denatured salmon sperm DNA, and 35% fonnamide.

9. The polypeptide of claim 8, which is encoded by a nucleic acid sequence which hybridizes under high stringency conditions with (i) nucleotides 55 to 1662 of SEQ ID NO:1, (ii) its complementary strand, or (iii) a subsequence thereof, wherein medium stringency conditions are defined as prehybridization and hybridization a 42° C. in 5×SSPE, 0.3% SDS, 200 mg/ml sheared and denatured salmon sperm DNA, and 50% formamide.

10. The polypeptide of claim 8, which is obtained from a strain of Aspergillus or teleomorph thereof.

11. The polypeptide of claim 10, which is obtained from a strain of *Aspergillus oryzae* or a teleomorph thereof.

12. The polypeptide of claim 1, which is encoded by the nucleic acid sequence contained in plasmid pEJG12 which is contained in *E. coli*, NRRL B-21616.

* * * * *

UNITED STATES PATENT AND TRADEMARK OFFICE
CERTIFICATE OF CORRECTION

PATENT NO. : 6,187,578 B1
DATED : February 13, 2001
INVENTOR(S) : Blinkovsky et al.

Page 1 of 1

It is certified that error appears in the above-identified patent and that said Letters Patent is hereby corrected as shown below:

Title page,
Item [73], delete "Bogsvoerd" and insert -- Bagsværd --

Column 59,
Line 58, delete "(A)" and insert -- (b) --

Signed and Sealed this

Nineteenth Day of February, 2002

Attest:

*Attesting Officer*

JAMES E. ROGAN
*Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 1662 base pairs
      (B) TYPE: nucleic acid
      (C) STRANDEDNESS: single
      (D) TOPOLOGY: linear (ii) MOLECULE TYPE: Genomic DNA (ix) FEATURE:
      (A) NAME/KEY: Coding Sequence
      (B) LOCATION: 1...1662
      (D) OTHER INFORMATION:

(xi) SEQUENCE DESCRIPTION: SEQ ID NO:1:

```
ATG CGT GGC TAC GAA TTT CTC TCA GTG CTA CCC TTG GTT GCA GCC AGT        48
Met Arg Gly Tyr Glu Phe Leu Ser Val Leu Pro Leu Val Ala Ala Ser
1               5                   10                  15

TGG GCC CTT CCA GGA AGT ACA CCG GCG TCC GTC GGT AGA AGA CAG CTA        96
Trp Ala Leu Pro Gly Ser Thr Pro Ala Ser Val Gly Arg Arg Gln Leu
                20                  25                  30

CCC AAG AAC CCC ACC GGG GTC AAG ACT CTT ACA ACC GCA AAC AAT GTC       144
Pro Lys Asn Pro Thr Gly Val Lys Thr Leu Thr Thr Ala Asn Asn Val
            35                  40                  45

ACC ATC CGG TAC AAG GAA CCC GGG GCA GAG GGC GTC TGC GAG ACT ACC       192
Thr Ile Arg Tyr Lys Glu Pro Gly Ala Glu Gly Val Cys Glu Thr Thr
    50                  55                  60

CCG GGT GTC AAA TCC TAC TCT GGA TAT GTC GAC ACC TCT CCC GAG TCC       240
Pro Gly Val Lys Ser Tyr Ser Gly Tyr Val Asp Thr Ser Pro Glu Ser
65                  70                  75                  80

CAT ACC TTC TTC TGG TTC TTC GAA GCC AGA CAT AAC CCA GAA ACT GCA       288
His Thr Phe Phe Trp Phe Phe Glu Ala Arg His Asn Pro Glu Thr Ala
                85                  90                  95

CCT ATC ACA TTG TGG TTG AAT GGT GGC CCT GGA AGC GAT TCT TTG ATC       336
Pro Ile Thr Leu Trp Leu Asn Gly Gly Pro Gly Ser Asp Ser Leu Ile
            100                 105                 110

GGT CTC TTC GAA GAG TTG GGC CCT TGC CAT GTC AAT TCG ACT TTT GAT       384
Gly Leu Phe Glu Glu Leu Gly Pro Cys His Val Asn Ser Thr Phe Asp
        115                 120                 125

GAC TAC ATC AAC CCT CAC TCG TGG AAC GAG GTC TCC AAT TTA CTA TTC       432
Asp Tyr Ile Asn Pro His Ser Trp Asn Glu Val Ser Asn Leu Leu Phe
    130                 135                 140

CTG TCC CAG CCA TTG GGA GTC GGC TTT TCA TAT AGT GAT ACG GTT GAT       480
```

```
                                          -continued

Leu Ser Gln Pro Leu Gly Val Gly Phe Ser Tyr Ser Asp Thr Val Asp
145                 150                 155                 160

GGG TCC ATT AAC CCT GTA ACT GGG GTC GTC GAA AAT TCG AGC TTT GCA           528
Gly Ser Ile Asn Pro Val Thr Gly Val Val Glu Asn Ser Ser Phe Ala
                165                 170                 175

GGA GTT CAG GGC CGG TAC CCA ACC ATT GAT GCC ACT CTG ATC GAT ACT           576
Gly Val Gln Gly Arg Tyr Pro Thr Ile Asp Ala Thr Leu Ile Asp Thr
            180                 185                 190

ACC AAT CTT GCC GCA GAG GCC GCT TGG GAG ATC CTG CAA GGA TTC CTT           624
Thr Asn Leu Ala Ala Glu Ala Ala Trp Glu Ile Leu Gln Gly Phe Leu
        195                 200                 205

AGT GGA CTA CCT AGC TTG GAC TCT AGG GTG CAG TCT AAG GAC TTC AGT           672
Ser Gly Leu Pro Ser Leu Asp Ser Arg Val Gln Ser Lys Asp Phe Ser
    210                 215                 220

CTA TGG ACG GAG AGC TAT GGA GGG CAC TAT GGT CCT GCA TTC TTC AAT           720
Leu Trp Thr Glu Ser Tyr Gly Gly His Tyr Gly Pro Ala Phe Phe Asn
225                 230                 235                 240

CAT TTT TAC GAG CAG AAT GAG AGA ATT GCC AAC GGT AGT GTT AAT GGT           768
His Phe Tyr Glu Gln Asn Glu Arg Ile Ala Asn Gly Ser Val Asn Gly
                245                 250                 255

GTT CAG CTT AAT TTC AAC TCT CTG GGA ATT ATT AAC GGC ATC ATC GAC           816
Val Gln Leu Asn Phe Asn Ser Leu Gly Ile Ile Asn Gly Ile Ile Asp
            260                 265                 270

GAG GCG ATC CAG GCC CCT TAC TAC CCT GAA TTC GCT GTG AAC AAT ACC           864
Glu Ala Ile Gln Ala Pro Tyr Tyr Pro Glu Phe Ala Val Asn Asn Thr
        275                 280                 285

TAC GGT ATC AAG GCT GTC AAC GAG ACC GTC TAC AAC TAC ATG AAG TTT           912
Tyr Gly Ile Lys Ala Val Asn Glu Thr Val Tyr Asn Tyr Met Lys Phe
    290                 295                 300

GCC AAC CAA ATG CCA AAT GGT TGC CAG GAT TTG ATT TCC ACC TGC AAA           960
Ala Asn Gln Met Pro Asn Gly Cys Gln Asp Leu Ile Ser Thr Cys Lys
305                 310                 315                 320

CAG ACA AAC CGC ACC GCA TTA GCT GAC TAC GCC CTC TGC GCC GAA GCC          1008
Gln Thr Asn Arg Thr Ala Leu Ala Asp Tyr Ala Leu Cys Ala Glu Ala
                325                 330                 335

ACC AAC ATG TGC AGG GAC AAT GTT GAG GGG CCA TAC TAC GCC TTT GCT          1056
Thr Asn Met Cys Arg Asp Asn Val Glu Gly Pro Tyr Tyr Ala Phe Ala
            340                 345                 350

GGT CGT GGT GTG TAT GAT ATT CGG CAT CCA TAT GAT GAC CCG ACT CCG          1104
Gly Arg Gly Val Tyr Asp Ile Arg His Pro Tyr Asp Asp Pro Thr Pro
        355                 360                 365

CCA AGT TAT TAC AAC AAA TTT CTG GCA AAG GAC TCT GTC ATG GAC GCT          1152
Pro Ser Tyr Tyr Asn Lys Phe Leu Ala Lys Asp Ser Val Met Asp Ala
    370                 375                 380

ATC GGC GTC AAC ATC AAC TAC ACC CAG TCC AAT AAT GAC GTC TAC TAC          1200
Ile Gly Val Asn Ile Asn Tyr Thr Gln Ser Asn Asn Asp Val Tyr Tyr
385                 390                 395                 400

GCT TTC CAG CAA ACA GGC GAC TTT GTC TGG CCC AAC TTC ATC GAA GAC          1248
Ala Phe Gln Gln Thr Gly Asp Phe Val Trp Pro Asn Phe Ile Glu Asp
                405                 410                 415

CTC GAG GAG ATC CTT GCT CTC CCC GTG CGT GTC TCC CTC ATC TAT GGC          1296
Leu Glu Glu Ile Leu Ala Leu Pro Val Arg Val Ser Leu Ile Tyr Gly
            420                 425                 430

GAC GCC GAT TAC ATC TGC AAC TGG TTC GGC GGT CAG GCC GTT TCC CTC          1344
Asp Ala Asp Tyr Ile Cys Asn Trp Phe Gly Gly Gln Ala Val Ser Leu
        435                 440                 445

GCT GCG AAC TAC TCC CAA GCC GCC CAG TTC CGA AGC GCA GGG TAC ACG          1392
Ala Ala Asn Tyr Ser Gln Ala Ala Gln Phe Arg Ser Ala Gly Tyr Thr
    450                 455                 460
```

```
CCC CTG AAA GTC AAC GGC GTC GAG TAT GGG GAA ACT CGC GAG TAT GGT        1440
Pro Leu Lys Val Asn Gly Val Glu Tyr Gly Glu Thr Arg Glu Tyr Gly
465                 470                 475                 480

AAT TTC TCC TTC ACT CGC GTC TAT GAG GCA GGC CAT GAA GTC CCA TAC        1488
Asn Phe Ser Phe Thr Arg Val Tyr Glu Ala Gly His Glu Val Pro Tyr
                485                 490                 495

TAC CAG CCC ATC GCC TCC CTG CAA TTG TTT AAC CGG ACT ATC TTC GGT        1536
Tyr Gln Pro Ile Ala Ser Leu Gln Leu Phe Asn Arg Thr Ile Phe Gly
            500                 505                 510

TGG GAT ATC GCA GAG GGC CAG AAG AAG ATC TGG CCC AGC TAC AAG ACG        1584
Trp Asp Ile Ala Glu Gly Gln Lys Lys Ile Trp Pro Ser Tyr Lys Thr
        515                 520                 525

AAT GGA ACG GCT ACA GCT ACG CAT ACA CAG TCG TCC GTG CCG CTG CCT        1632
Asn Gly Thr Ala Thr Ala Thr His Thr Gln Ser Ser Val Pro Leu Pro
    530                 535                 540

ACG GCT ACC AGC ATG TCC AGT GTT GGT ATG                                1662
Thr Ala Thr Ser Met Ser Ser Val Gly Met
545                 550
```

(2) INFORMATION FOR SEQ ID NO:2:

(i) SEQUENCE CHARACTERISTICS:
        (A) LENGTH: 554 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Arg Gly Tyr Glu Phe Leu Ser Val Leu Pro Leu Val Ala Ala Ser
1               5                   10                  15

Trp Ala Leu Pro Gly Ser Thr Pro Ala Ser Val Gly Arg Arg Gln Leu
                20                  25                  30

Pro Lys Asn Pro Thr Gly Val Lys Thr Leu Thr Thr Ala Asn Asn Val
            35                  40                  45

Thr Ile Arg Tyr Lys Glu Pro Gly Ala Glu Gly Val Cys Glu Thr Thr
        50                  55                  60

Pro Gly Val Lys Ser Tyr Ser Gly Tyr Val Asp Thr Ser Pro Glu Ser
65                  70                  75                  80

His Thr Phe Phe Trp Phe Phe Glu Ala Arg His Asn Pro Glu Thr Ala
                85                  90                  95

Pro Ile Thr Leu Trp Leu Asn Gly Gly Pro Gly Ser Asp Ser Leu Ile
            100                 105                 110

Gly Leu Phe Glu Glu Leu Gly Pro Cys His Val Asn Ser Thr Phe Asp
        115                 120                 125

Asp Tyr Ile Asn Pro His Ser Trp Asn Glu Val Ser Asn Leu Leu Phe
    130                 135                 140

Leu Ser Gln Pro Leu Gly Val Gly Phe Ser Tyr Ser Asp Thr Val Asp
145                 150                 155                 160

Gly Ser Ile Asn Pro Val Thr Gly Val Val Glu Asn Ser Ser Phe Ala
                165                 170                 175

Gly Val Gln Gly Arg Tyr Pro Thr Ile Asp Ala Thr Leu Ile Asp Thr
            180                 185                 190

Thr Asn Leu Ala Ala Glu Ala Ala Trp Glu Ile Leu Gln Gly Phe Leu
        195                 200                 205

Ser Gly Leu Pro Ser Leu Asp Ser Arg Val Gln Ser Lys Asp Phe Ser
```

-continued

```
              210                 215                 220
Leu Trp Thr Glu Ser Tyr Gly Gly His Tyr Gly Pro Ala Phe Phe Asn
225                 230                 235                 240

His Phe Tyr Glu Gln Asn Glu Arg Ile Ala Asn Gly Ser Val Asn Gly
                245                 250                 255

Val Gln Leu Asn Phe Asn Ser Leu Gly Ile Ile Asn Gly Ile Ile Asp
                260                 265                 270

Glu Ala Ile Gln Ala Pro Tyr Tyr Pro Glu Phe Ala Val Asn Asn Thr
                275                 280                 285

Tyr Gly Ile Lys Ala Val Asn Glu Thr Val Tyr Asn Tyr Met Lys Phe
                290                 295                 300

Ala Asn Gln Met Pro Asn Gly Cys Gln Asp Leu Ile Ser Thr Cys Lys
305                 310                 315                 320

Gln Thr Asn Arg Thr Ala Leu Ala Asp Tyr Ala Leu Cys Ala Glu Ala
                325                 330                 335

Thr Asn Met Cys Arg Asp Asn Val Glu Gly Pro Tyr Tyr Ala Phe Ala
                340                 345                 350

Gly Arg Gly Val Tyr Asp Ile Arg His Pro Tyr Asp Asp Pro Thr Pro
                355                 360                 365

Pro Ser Tyr Tyr Asn Lys Phe Leu Ala Lys Asp Ser Val Met Asp Ala
370                 375                 380

Ile Gly Val Asn Ile Asn Tyr Thr Gln Ser Asn Asn Asp Val Tyr Tyr
385                 390                 395                 400

Ala Phe Gln Gln Thr Gly Asp Phe Val Trp Pro Asn Phe Ile Glu Asp
                405                 410                 415

Leu Glu Glu Ile Leu Ala Leu Pro Val Arg Val Ser Leu Ile Tyr Gly
                420                 425                 430

Asp Ala Asp Tyr Ile Cys Asn Trp Phe Gly Gly Gln Ala Val Ser Leu
                435                 440                 445

Ala Ala Asn Tyr Ser Gln Ala Ala Gln Phe Arg Ser Ala Gly Tyr Thr
450                 455                 460

Pro Leu Lys Val Asn Gly Val Glu Tyr Gly Thr Arg Glu Tyr Gly
465                 470                 475                 480

Asn Phe Ser Phe Thr Arg Val Tyr Glu Ala Gly His Glu Val Pro Tyr
                485                 490                 495

Tyr Gln Pro Ile Ala Ser Leu Gln Leu Phe Asn Arg Thr Ile Phe Gly
                500                 505                 510

Trp Asp Ile Ala Glu Gly Gln Lys Lys Ile Trp Pro Ser Tyr Lys Thr
                515                 520                 525

Asn Gly Thr Ala Thr Ala Thr His Thr Gln Ser Ser Val Pro Leu Pro
                530                 535                 540

Thr Ala Thr Ser Met Ser Ser Val Gly Met
545                 550
```

(2) INFORMATION FOR SEQ ID NO:3:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

Xaa Tyr Gly Gly His Tyr Gly Pro Ala Phe Phe Asn His Phe Tyr Glu

```
            1               5              10              15

Gln Asn Glu Arg
            20

(2) INFORMATION FOR SEQ ID NO:4:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

Asp Ala Ile Gly Val Asn Ile Xaa Tyr Thr Gln Xaa Asn Asn Asp Val
 1               5                  10                  15

Tyr Tyr Ala (2) INFORMATION FOR SEQ ID NO:5:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

Asp Ala Ile Gly Val Asn Ile Asn Tyr Thr Gln Ser Asn Asn Asp Val
 1               5                  10                  15

Tyr Tyr Ala Phe Gln Gln Thr Gly Asp Phe Val Trp Pro Asn Phe Ile
                20                  25                  30

Glu Asp Leu
        35

(2) INFORMATION FOR SEQ ID NO:6:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

Xaa Cys Arg Asp Asn Val Glu Gly Pro Xaa Tyr Ala Phe Ala Gly Arg
 1               5                  10                  15

Gly Val Tyr Asp Ile Arg His Pro Tyr Asp Pro Asp Thr
                20                  25

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

TAYGGNGGCA YTAYGGCCNG                                           20

(2) INFORMATION FOR SEQ ID NO:8:
```

```
        (i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:8:

ATRAARTTGG CCAACRAART C                                               21

(2) INFORMATION FOR SEQ ID NO:9:

(i) SEQUENCE CHARACTERISTICS:
            (A) LENGTH: 423 amino acids
            (B) TYPE: amino acid
            (C) STRANDEDNESS: single
            (D) TOPOLOGY: linear (xi) SEQUENCE DESCRIPTION: SEQ ID NO:9:

Phe Val Lys Asn Ser Gly Ile Cys Glu Thr Thr Pro Gly Val Asn Gln
 1               5                  10                  15

Tyr Ser Gly Tyr Leu Ser Val Gly Ser Asn Met Asn Met Trp Phe Trp
            20                  25                  30

Phe Phe Glu Ala Arg Asn Asn Pro Gln Gln Ala Pro Leu Ala Ala Trp
        35                  40                  45

Phe Asn Gly Gly Pro Gly Cys Ser Ser Met Ile Gly Leu Phe Gln Glu
 50                  55                  60

Asn Gly Pro Cys His Phe Val Asn Gly Asp Ser Thr Pro Ser Leu Asn
65                  70                  75                  80

Glu Asn Ser Trp Asn Asn Tyr Ala Asn Met Ile Tyr Ile Asp Gln Pro
                85                  90                  95

Ile Gly Val Gly Phe Ser Tyr Gly Thr Asp Asp Val Thr Ser Thr Val
            100                 105                 110

Thr Ala Ala Pro Tyr Val Trp Asn Leu Leu Gln Ala Phe Tyr Ala Gln
        115                 120                 125

Arg Pro Glu Tyr Glu Ser Arg Asp Phe Ala Ile Phe Thr Glu Ser Tyr
    130                 135                 140

Gly Gly His Tyr Gly Pro Glu Phe Ala Ser Tyr Ile Glu Gln Gln Asn
145                 150                 155                 160

Ala Ala Ile Lys Ala Gly Ser Val Thr Gly Gln Asn Val Asn Ile Val
                165                 170                 175

Ala Leu Gly Val Asn Asn Gly Trp Ile Asp Ser Thr Ile Gln Glu Lys
            180                 185                 190

Ala Tyr Ile Asp Phe Ser Tyr Asn Asn Ser Tyr Gln Gln Ile Ile Asp
        195                 200                 205

Ser Ser Thr Arg Asp Ser Leu Leu Asp Ala Tyr Asn Asn Gln Cys Leu
    210                 215                 220

Pro Ala Leu Gln Gln Cys Ser Gln Ser Gly Ser Thr Ser Asp Cys Thr
225                 230                 235                 240

Asn Ala Asp Ser Val Cys Tyr Gln Asn Ile Glu Gly Pro Ile Ser Ser
                245                 250                 255

Ser Gly Asp Phe Asp Val Tyr Asp Ile Arg Glu Pro Ser Asn Asp Pro
            260                 265                 270

Tyr Pro Pro Lys Thr Tyr Ser Thr Tyr Leu Ser Asp Pro Thr Val Val
        275                 280                 285

Lys Ala Ile Gly Ala Arg Thr Asn Tyr Gln Glu Cys Pro Asn Gly Pro
```

-continued

```
                 290                 295                 300
Tyr Asn Lys Phe Ala Ser Thr Gly Asp Asn Pro Arg Ser Phe Leu Ser
305                 310                 315                 320

Thr Leu Ser Ser Val Val Gln Ser Gly Ile Asn Val Leu Val Trp Ala
                325                 330                 335

Gly Asp Ala Asp Trp Ile Cys Asn Trp Leu Gly Asn Tyr Glu Val Ala
                340                 345                 350

Asn Ala Val Asp Phe Pro Gly Asn Ala Gln Phe Ser Ala Leu Asp Leu
                355                 360                 365

Ala Pro Tyr Thr Val Asn Gly Val Glu Lys Gly Gln Phe Lys Thr Val
                370                 375                 380

Asp Asn Phe Ser Phe Leu Lys Val Tyr Gly Ala Gly His Glu Val Pro
385                 390                 395                 400

Tyr Tyr Gln Pro Asp Thr Ala Leu Gln Ala Phe Lys Gln Ile Ile Gln
                405                 410                 415

Lys Lys Pro Ile Ser Ser Thr
                420
```

(2) INFORMATION FOR SEQ ID NO:10:

(i) SEQUENCE CHARACTERISTICS:
        (A) LENGTH: 481 amino acids
        (B) TYPE: amino acid
        (C) STRANDEDNESS: single
        (D) TOPOLOGY: linear (xi) SEQUENCE DESCRIPTION: SEQ ID NO:10:

```
Ser Thr Lys Asn Tyr Arg Phe Leu Asn Glu Lys Thr Lys Ala Asn Leu
1                 5                  10                  15

Val His His Leu Pro Asp Val Pro Tyr Asp Ile Gly Glu Met Tyr Ser
                20                  25                  30

Gly Leu Met Pro Ile Asp Met His Asn Glu Ser Arg Ala Leu Phe Tyr
                35                  40                  45

Ile Phe Gln Pro Thr Ile Gly Glu Pro Val Asp Glu Val Thr Ile Trp
50                  55                  60

Met Asn Gly Gly Pro Gly Cys Ser Ser Met Glu Ser Phe Leu Gln Glu
65                  70                  75                  80

Thr Gly Arg Phe Leu Trp Gln Pro Gly Thr Tyr Ala Pro Val Glu Asn
                85                  90                  95

Pro Tyr Ser Trp Val Val Leu Thr Asn Val Leu Trp Val Asp Gln Pro
                100                 105                 110

Val Gly Thr Gly Tyr Ser Ile Gly Thr Pro Thr Ala Thr Ser Gln Glu
                115                 120                 125

Glu Thr Ala Gln Asp Phe Val Lys Phe Phe Lys Asn Phe Gln Lys Thr
130                 135                 140

Tyr Gly Ile Lys Asn Phe Lys Ile Tyr Val Thr Gly Glu Ser Tyr Ala
145                 150                 155                 160

Gly Arg Tyr Val Pro Tyr Ile Ser Ala Ala Met Leu Asp Glu Lys Asp
                165                 170                 175

Lys Glu Tyr Phe Asp Leu Gln Gly Ala Leu Ala Tyr Asp Pro Cys Ile
                180                 185                 190

Gly Gln Phe Asp Tyr Val Gln Glu Glu Ile Pro Val Val Pro Phe Val
                195                 200                 205

Lys Glu Asn Ala Asn Leu Phe Asn Phe Asn Glu Thr Phe Met Ala Glu
                210                 215                 220
```

```
Leu Glu His Leu His Lys Ser Cys Gly Tyr Ala Asp Phe Ile Asp Lys
225                 230                 235                 240

Tyr Leu Thr Phe Pro Pro Lys Glu Gln Pro Pro Leu Phe Phe Asn
            245                 250                 255

Tyr Thr Ser Met Ala Asn Glu Asp Val Phe Asp Met Val Tyr Asn Glu
            260                 265                 270

Val Phe Lys Ile Asn Pro Cys Phe Asp Leu Tyr Glu Val Asn Leu Met
            275                 280                 285

Cys Pro Leu Gln Trp Asp Val Leu Ala Phe Pro Thr Ser Leu Val Tyr
            290                 295                 300

Gln Pro Ala Gly Ala Thr Val Tyr Phe Asp Arg Ala Asp Val Lys Lys
305                 310                 315                 320

Ala Leu His Ala Pro Asn Val Thr Trp Ala Glu Cys Ser Asn Asn Pro
            325                 330                 335

Val Phe Val Gly Gly Ser Ser Gly Pro Glu Gln Glu Gly Asp Thr Ser
            340                 345                 350

Ala Asn Pro Ile Glu His Val Leu Pro Gln Val Ile Glu Ala Thr Asn
            355                 360                 365

Arg Val Leu Ile Ser Asn Gly Asp Phe Asp Met Val Ile Leu Thr Asn
            370                 375                 380

Gly Thr Leu Leu Ala Ile Gln Asn Met Thr Trp Asn Gly His Leu Gly
385                 390                 395                 400

Phe Gln Lys Lys Pro Ser Ala Pro Ile Asp Ile Lys Ile Pro Asp Leu
            405                 410                 415

Gln Tyr Lys Glu Val Phe Ala Glu Asn Gly Ala Ser Ser Leu Asp Gly
            420                 425                 430

Ala Gln Gly Ile Met Gly Val Gln His Tyr Glu Arg Gly Leu Met Lys
            435                 440                 445

Ala Gln Thr Tyr Gln Ser Gly His Met Gln Pro Gln Tyr Gln Pro Arg
            450                 455                 460

Val Ala Tyr Arg His Leu Glu Trp Leu Leu Lys Arg Thr Asp Glu Leu
465                 470                 475                 480

Gln
```

(2) INFORMATION FOR SEQ ID NO:11:

(i) SEQUENCE CHARACTERISTICS:
        (A) LENGTH: 523 amino acids
        (B) TYPE: amino acid
        (C) STRANDEDNESS: single
        (D) TOPOLOGY: linear (xi) SEQUENCE DESCRIPTION: SEQ ID NO:11:

```
Met Arg Ile Thr Ser Ala Ile Ala Ser Leu Leu Leu Val Gly Thr Ala
1               5                   10                  15

Thr Ser Leu Gln Asn Pro His Arg Arg Ala Val Pro Ala Pro Leu Thr
            20                  25                  30

His Arg Ser Val Ala Ser Arg Ala Val Pro Val Glu Arg Arg Ser Asn
            35                  40                  45

Asp Phe Glu Tyr Leu Thr Asn Lys Thr Ala Arg Phe Leu Val Asn Gly
50                  55                  60

Thr Ser Ile Pro Glu Val Asp Phe Asp Val Gly Glu Ser Tyr Ala Gly
65                  70                  75                  80

Leu Leu Pro Asn Thr Pro Thr Gly Asn Ser Ser Leu Phe Phe Trp Phe
            85                  90                  95
```

```
Phe Pro Ser Gln Asn Pro Asp Ala Ser Asp Glu Ile Thr Ile Trp Leu
            100                 105                 110
Asn Gly Gly Pro Gly Cys Ser Ser Leu Asp Gly Leu Leu Gln Glu Asn
            115                 120                 125
Gly Pro Phe Leu Trp Gln Pro Gly Thr Tyr Lys Pro Val Pro Asn Pro
            130                 135                 140
Tyr Ser Trp Thr Asn Leu Thr Asn Val Val Tyr Ile Asp Gln Pro Ala
145                 150                 155                 160
Gly Thr Gly Phe Ser Pro Gly Pro Ser Thr Val Asn Asp Glu Asp
            165                 170                 175
Val Ala Ala Gln Phe Asn Ser Trp Phe Lys His Phe Val Asp Thr Phe
            180                 185                 190
Asp Leu His Gly Arg Lys Val Tyr Ile Thr Gly Glu Ser Tyr Ala Gly
            195                 200                 205
Met Tyr Val Pro Tyr Ile Ala Asp Ala Met Leu Asn Glu Glu Asp Thr
            210                 215                 220
Thr Tyr Phe Asn Leu Lys Gly Ile Gln Ile Asn Asp Pro Ser Ile Asn
225                 230                 235                 240
Ser Asp Ser Val Met Met Tyr Ser Pro Ala Val Arg His Leu Asn His
            245                 250                 255
Tyr Asn Asn Ile Phe Arg Leu Asn Ser Thr Phe Leu Ser Tyr Ile Asn
            260                 265                 270
Gly Lys Ala Asp Lys Cys Gly Tyr Asn Ala Phe Leu Asp Lys Ala Ile
            275                 280                 285
Thr Tyr Pro Pro Pro Thr Pro Phe Pro Thr Ala Pro Glu Ile Thr Glu
            290                 295                 300
Asp Cys Gln Val Trp Asp Glu Val Val Met Ala Ala Tyr Asp Ile Asn
305                 310                 315                 320
Pro Cys Phe Asn Tyr Tyr His Leu Ile Asp Phe Cys Pro Tyr Leu Trp
            325                 330                 335
Asp Val Leu Gly Phe Pro Ser Leu Gly Phe Gly Pro Asp Asn Tyr Phe
            340                 345                 350
Asn Arg Ser Asp Val Gln Lys Ile Leu His Val Pro Pro Thr Asp Tyr
            355                 360                 365
Ser Val Cys Ser Glu Thr Val Ile Phe Ala Asn Gly Asp Gly Ser Asp
            370                 375                 380
Pro Ser Ser Trp Gly Pro Leu Pro Ser Val Ile Glu Arg Thr Asn Asn
385                 390                 395                 400
Thr Ile Ile Gly His Gly Trp Leu Asp Tyr Leu Leu Phe Leu Asn Gly
            405                 410                 415
Ser Leu Ala Thr Ile Gln Asn Met Thr Trp Asn Gly Lys Gln Gly Phe
            420                 425                 430
Gln Ser Pro Pro Val Glu Pro Leu Phe Val Pro Tyr His Tyr Gly Leu
            435                 440                 445
Ala Glu Leu Tyr Trp Gly Asp Glu Pro Asp Pro Tyr Asn Leu Asp Ala
450                 455                 460
Gly Ala Gly Tyr Leu Gly Thr Ala His Thr Glu Arg Gly Leu Thr Phe
465                 470                 475                 480
Ser Ser Val Tyr Leu Ser Gly His Glu Ile Pro Gln Tyr Val Pro Gly
            485                 490                 495
Ala Leu Thr Ala Ser Trp Ser Ser Cys Leu Val Glu Leu Ile Val Phe
            500                 505                 510
Pro Arg Arg Gly Thr Thr Pro Leu Asn Phe Ser
```

(2) INFORMATION FOR SEQ ID NO:12:

(i) SEQUENCE CHARACTERISTICS:
        (A) LENGTH: 530 amino acids
        (B) TYPE: amino acid
        (C) STRANDEDNESS: single
        (D) TOPOLOGY: linear (xi) SEQUENCE DESCRIPTION: SEQ ID NO:12:

```
Met Leu Phe Arg Ser Leu Leu Ser Thr Ala Val Leu Ala Val Ser Leu
  1               5                  10                  15

Cys Thr Asp Asn Ala Ser Ala Ala Lys His Gly Arg Phe Gly Gln Lys
                 20                  25                  30

Ala Arg Asp Ala Met Asn Ile Ala Asn Gly Ser Ala Asn Ala Val Lys
             35                  40                  45

His Ser Leu Lys Ile Pro Val Glu Asp Tyr Gln Phe Leu Asn Asn Lys
         50                  55                  60

Thr Lys Pro Tyr Arg Val Glu Ser Leu Pro Asp Val His Phe Asp Leu
 65                  70                  75                  80

Gly Glu Met Tyr Ser Gly Leu Val Pro Ile Glu Lys Gly Asn Val Ser
                 85                  90                  95

Arg Ser Leu Phe Phe Val Phe Gln Pro Thr Ile Gly Glu Pro Val Asp
                100                 105                 110

Glu Thr Thr Ile Trp Leu Asn Gly Gly Pro Gly Cys Ser Ser Leu Glu
            115                 120                 125

Ala Leu Ser Pro Gly Glu Cys Arg Phe Val Trp Gln Pro Gly Thr Tyr
        130                 135                 140

Gln Pro Val Glu Asn Pro Tyr Ser Trp Val Asn Leu Thr Asn Val Leu
145                 150                 155                 160

Trp Val Asp Gln Pro Val Gly Thr Gly Phe Ser Leu Gly Val Pro Thr
                165                 170                 175

Ala Thr Ser Glu Glu Glu Ile Ala Glu Asp Phe Val Lys Phe Phe Lys
            180                 185                 190

Asn Trp Gln Gln Ile Phe Gly Ile Lys Asn Phe Lys Ile Tyr Val Thr
        195                 200                 205

Gly Glu Ser Tyr Ala Gly Arg Tyr Val Pro Tyr Ile Ser Ala Ala Phe
    210                 215                 220

Leu Asp Gln Asn Asp Thr Glu His Phe Asn Leu Lys Gly Ala Leu Ala
225                 230                 235                 240

Tyr Asp Pro Cys Ile Gly Gln Phe Asp Tyr Val Gln Glu Glu Ala Pro
                245                 250                 255

Val Val Pro Phe Val Gln Lys Asn Asn Ala Leu Phe Asn Phe Asn Ala
            260                 265                 270

Ser Phe Leu Ala Glu Leu Glu Ser Ile His Glu Gln Cys Gly Tyr Lys
        275                 280                 285

Asp Phe Ile Asp Gln Tyr Leu Val Phe Pro Ala Ser Gly Val Gln Pro
    290                 295                 300

Pro Lys Ala Met Asn Trp Ser Asp Pro Thr Cys Asp Val Tyr Asp Ile
305                 310                 315                 320

Val Asn Asn Ala Val Leu Asp Pro Asn Pro Cys Phe Asn Pro Tyr Glu
                325                 330                 335

Ile Asn Glu Met Cys Pro Ile Leu Trp Asp Val Leu Gly Phe Pro Thr
            340                 345                 350
```

-continued

```
Glu Val Asp Tyr Leu Pro Ala Ala Pro Ala Ser Thr Leu Thr Ala Leu
            355                 360                 365

Ile Lys Arg Ala Met His Ala Pro Asn Ile Thr Trp Ser Glu Cys Ser
    370                 375                 380

Val Glu Ser Val Phe Val Gly Gly Asp Gly Gly Pro Glu Gln Glu Gly
385                 390                 395                 400

Asp Tyr Ser Ala Asn Pro Ile Glu His Val Leu Pro Gln Val Ile Glu
                405                 410                 415

Gly Thr Asn Arg Val Leu Ile Gly Asn Gly Asp Tyr Asp Met Val Ile
                420                 425                 430

Leu Thr Asn Gly Thr Leu Leu Ser Ile Gln Asn Met Thr Trp Asn Gly
            435                 440                 445

Lys Leu Gly Phe Asp Thr Ala Pro Ser Thr Pro Ile Asn Ile Asp Ile
    450                 455                 460

Pro Asp Leu Met Tyr Asn Glu Val Phe Ile Glu Asn Gly Tyr Asp Pro
465                 470                 475                 480

Gln Gly Gly Gln Gly Val Met Gly Ile Gln His Tyr Glu Arg Gly Leu
                485                 490                 495

Met Trp Ala Glu Thr Phe Gln Ser Gly His Met Gln Pro Gln Phe Gln
                500                 505                 510

Pro Arg Val Ser Tyr Arg His Leu Glu Trp Leu Leu Gly Arg Arg Asp
            515                 520                 525

Thr Leu
    530
```